United States Patent
Navakatikyan et al.

(10) Patent No.: US 7,353,127 B2
(45) Date of Patent: Apr. 1, 2008

(54) APPARATUS AND METHOD FOR DETECTION AND QUANTIFICATION OF OSCILLATORY SIGNALS

(75) Inventors: Michael Alexander Navakatikyan, Auckland (NZ); Simon Charles Malpas, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 447 days.

(21) Appl. No.: 10/471,170

(22) PCT Filed: Mar. 8, 2002

(86) PCT No.: PCT/NZ02/00029

§ 371 (c)(1), (2), (4) Date: Dec. 9, 2003

(87) PCT Pub. No.: WO02/071936

PCT Pub. Date: Sep. 19, 2002

(65) Prior Publication Data

US 2004/0097814 A1   May 20, 2004

(30) Foreign Application Priority Data

Mar. 9, 2001   (NZ) .................................. 510459

(51) Int. Cl.
  *G01R 23/00*   (2006.01)
  *A61B 5/04*   (2006.01)
(52) U.S. Cl. ............................ 702/79; 702/75; 702/19; 600/519

(58) Field of Classification Search ................. 702/66, 702/72, 75, 79, 189, 190, 199; 600/485, 600/493, 494, 495, 500, 501, 504, 505, 508, 600/509, 519, 521, 523; 324/103 P, 76.12, 324/76.13, 76.15, 76.19, 76.22, 76.24, 76.37, 324/76.39
See application file for complete search history.

(56) References Cited

U.S. PATENT DOCUMENTS

| | | | |
|---|---|---|---|
| 4,223,682 A | | 9/1980 | Sherman |
| 5,065,766 A | | 11/1991 | Sasaki |
| 5,170,795 A | | 12/1992 | Ramsey, III et al. |
| 5,274,548 A | | 12/1993 | Bernard et al. |
| 5,339,820 A | | 8/1994 | Henry et al. |
| 5,385,149 A | * | 1/1995 | Chang et al. ............... 600/493 |

* cited by examiner

*Primary Examiner*—Manuel L Barbee
(74) *Attorney, Agent, or Firm*—Darby & Darby P.C.

(57) ABSTRACT

A method of determining the location in time of maxima and/or minima of an oscillatory signal. The method may have application to measurement of biological signals, in particular measurement of heart rate from a pulsatile blood signal. The method includes a first stage including the steps of observation over a measurement period, identifying large local maxima or minima and computing an average interval between the identified local maxima or minima. One or more exclusion periods are located in time in the oscillatory signal, having a duration dependent on the average interval, the exclusion periods used to reject false maxima or minima. Maxima or minima may also be detected as an absolute maximum or minimum between crossing points of a fast and a slow moving average of the oscillatory signal. An exclusion period may also be used to reject false maxima or minima when crossing points are used. Apparatus for performing the method is also claimed.

26 Claims, 24 Drawing Sheets intervals, ms
346
590
394
340

Median Interval=370 intervals, ms
282
270
480
246
238
238

Median Interval=258 intervals, ms
222
256
200
460
452
240

Median Interval=248

APPARATUS AND METHOD FOR DETECTION AND QUANTIFICATION OF OSCILLATORY SIGNALS

TECHNICAL FIELD

This invention relates to a method and apparatus for detection and quantification of oscillatory signals.

In particular, but not exclusively, this invention relates to a method and apparatus for detection and quantification of oscillatory biological signals, with application to the detection of blood pressure and identification of periodic maxima or minima of the blood pressure waveform. Once the periodic maxima or minima have been identified, characteristics of the blood pressure waveform including the frequency, may be identified.

BACKGROUND TO THE INVENTION

Many signals have oscillatory characteristics, ranging from a simple sine wave to noisy signals which may vary greatly in frequency and amplitude over time. Biological signals often display oscillatory characteristics and are generally prone to noise, either inherent in the signal and/or in the measuring apparatus and some are also liable to large and rapid regular or irregular fluctuations in their frequency and amplitude.

Thus, measurement of signals like biological signals often gives rise to false positive or negative detection of the measured characteristic when traditional methods of detection based on constant thresholds are used. Such false detection's lead to inaccuracies in the measurement of the characteristics of the signal.

One area where inaccuracies in the measurement of the signal may be particularly onerous is in the detection of heart beats. Heart beats are typically monitored in hospitals or the like where it is necessary to monitor the functions of the heart for diagnosis purposes or to give an indication when a patient requires medical attention. However, heart rate is also often monitored to assist in the evaluation of the performance of athletes, to monitor stress levels of individuals in certain situations and have been used to give an indication of whether someone is being untruthful. However, the most critical detection process is usually monitoring a patient in a care situation.

Heart beats may be detected by monitoring the pulsatile blood pressure signal. However, the blood pressure signal reflects the fact that rapid changes in heart rate can occur within a single beat, which can give rise to false positive or false negative detection of a heart beat. For example, in the case of pulse arrhythmia, there is varying (often regularly) beat-to-beat interval and amplitude, which need not be rejected during the detection. In addition, depending on the measurement site, the pulse wave often contains significant amounts of wave reflection, which must be accommodated for in order to accurately detect each heart beat and not to be mistaken for the irregular variations of frequency and amplitude during arrhythmia.

Problems similar to distinguishing between variations of the blood pressure signal over time due to arrhythmia, reflections and changes in amplitude, frequency and baseline are often present in biological signals and in other oscillatory signals which exhibit highly variable and or noisy characteristics. These variations cause significant difficulties in accurately measuring the characteristics of the signal such as frequency and amplitude.

OBJECT OF THE INVENTION

Thus, it is an object of this invention to provide a method and apparatus for detection and quantification of variable oscillatory signals which has increased accuracy or one which overcomes or alleviates problems in methods and apparatus for detection at present or at least one which provides the public with a useful alternative.

Further objects of the present invention may become apparent from the following description, given by way of example only and with reference to the accompanying drawings.

SUMMARY OF THE INVENTION

According to a first aspect of the invention, there is provided a method of determining the location in time of maxima and/or minima of an oscillatory signal, the method including the steps of:

i) observing the amplitude of the oscillatory signal over a predefined measurement period and identifying local maxima or minima that have a preselected measure indicative of the size of the maxima or minima, which exceeds a certain threshold;

ii) computing an average interval between local maxima or minima identified in step i);

iii) computing the duration of one or more exclusion periods dependent on said average interval;

iv) determining a location in time of the one or more exclusion periods based on the observed signal;

v) detecting local maxima or minima in the observed signal and rejecting a maximum or minimum if a maximum or minimum is located in time within an exclusion period.

Preferably, the certain threshold is calculated as a predetermined proportion of said preselected measure of the local maximum or minimum that has the greatest size according to said preselected measure.

Preferably, the preselected measure indicative of the size of the maxima or minima may be either the amplitude of the maxima or minima, or the magnitude of the fall or rise to an adjacent minimum or maximum respectively.

Preferably, the duration of the one or more exclusion periods may be a predetermined percentage or proportion of said average interval.

Preferably, the location in time of an exclusion period may be dependent on the location in time of a crossing point between two moving averages having different averaging intervals.

Preferably, the location in time of an exclusion period may be dependent on the location in time of a previously calculated maximum or minimum.

Preferably, the averaging interval of each moving average may be updated dependent on said average interval.

According to a second aspect of the invention, there is provided a method of determining the location in time of periodic maxima and/or minima of an oscillatory signal, the method including the steps of:

a) observing the oscillatory signal by detecting the amplitude of the oscillatory signal;

b) computing a first and a second moving average of the oscillatory signal, the first moving average having a first averaging time interval and the second moving average having a second averaging time interval longer than the first averaging time interval;

c) determining the location in time of a plurality of crossing points, wherein a crossing point is a point of intersection between the first and second moving averages;

d) defining at least one measurement period as the interval between two crossing points; and e) determining the location in time of an absolute maximum or minimum of the oscillatory signal within the or each measurement period, thereby determining the location in time of each periodic maxima or minima respectively of the oscillatory signal.

Preferably, a crossing point is defined as a first type if the first moving average was less than the second moving average prior to the crossing point and defined as a second type if the first moving average was greater than the second moving average prior to the crossing point and wherein the measurement period may be defined as the interval between two consecutive crossing points of the same type.

Preferably, a crossing point is defined as a first type if the first moving average was less than the second moving average prior to the crossing point and defined as a second type if the first moving average was greater than the second moving average prior to the crossing point and wherein the measurement period may be defined as the interval between two consecutive crossing points of a different type.

Preferably, the method may further include the steps of:

f) defining an exclusion period located in time relative to at least one of each crossing point defining each measurement period;

g) evaluating whether a crossing point defining a first measurement period falls within an exclusion period corresponding to a crossing point defining a second measurment period; and h) if the crossing point defining the first measurement period falls within the exclusion period corresponding to the crossing point defining the second measurement period, evaluating whether that crossing point or the crossing point corresponding to the exclusion period within which it is located in time satisfies a first predetermined set of criteria and rejecting the crossing point for the purposes of defining a measurement period if said criteria are met.

Preferably, if a crossing point is rejected, the method may further include also rejecting the exclusion period associated with the rejected crossing point.

Preferably, the method may further include the steps of:

i) detecting the location in time of a plurality of local maxima or minima within the oscillatory signal that exceed a predetermined amplitude threshold; and j) computing the length of the exclusion period in time dependent on an average value of the separation in time of detected maxima or minima that exceed said predetermined amplitude threshold.

Preferably, the method may further include rejecting a local maximum detected in step i) for the purposes of step j) if the local maximum falls within a predetermined time period of a local maximum having a greater value.

Preferably, the method may further include rejecting a local minimum detected in step i) for the purposes of step j) if the local minimum falls within a predetermined time period of a local minimum having a lesser value.

Preferably, the average value of the separation in time of detected maxima or minima may be a median value.

Preferably, the method may further include band-pass filtering the observed signal prior to performing step i).

Preferably, the predetermined amplitude threshold may be computed using the equation: $Thr=(Max_F-Avg_F) \cdot f_1 + Avg_F$ if maxima is determined in step e) and using the equation $Thr=(Min_F-Avg_F) \cdot f_1 + Avg_F$ if minima is determined in step e), wherein Thr is the predetermined threshold, $Avg_F$ is an average of the observed signal, $Max_F$ is the maximum of the observed signal, $Min_F$ is the minimum of the observed signal, and $f_1$ is a preset fraction dependent on the characteristics of the signal and wherein $Avg_F$, $Max_F$, and $Min_F$ are determined from a sample of the observed signal.

Preferably, step f) may include locating the exclusion period immediately adjacent to the crossing point, after the crossing point.

Preferably, the method may further include comparing an average value of the observed signal over a sample period with the maximum and minimum values over the same sample period and inverting the signal if required so that the maximum or minimum determined in step e) has a greater variation from the average than the minimum or maximum respectively.

Preferably, the reflected or inverted signal may be computed as double an average of the observed signal less the value of the observed signal.

Preferably, the method may further include defining an exclusion period located in time relative to a detected maximum or minimum within each measurement period and evaluating whether a detected maximum or minimum of a first measurement period falls within an exclusion period corresponding to a maximum or minimum of a second measurement period and if the maximum or minimum of the first measurement period falls within the exclusion period of the second measurement period, evaluating whether the crossing point corresponding t the maximum or minimum of the first measurement period or the crossing point corresponding to the exclusion period within which the maximum or minimum of the first measurement period falls satisfies a predetermined set of criteria and rejecting a crossing point for the purposes of defining a measurement period if said criteria are met.

Preferably, the set of predetermined criteria may be based on the relative magnitude of a maximum or minimum in an exclusion period to the magnitude of at least one maximum or minimum respectively in the observed signal.

Preferably, a crossing point may be rejected if the amplitude of a maximum within the measurement period defined by that crossing point is less than an adjacent maximum or less than a predetermined percentage of an adjacent maximum.

Preferably, a crossing point may rejected if the amplitude of the corresponding minimum to the crossing point located within the exclusion period is greater than an adjacent minimum or greater than a percentage of an adjacent minimum.

Preferably, a crossing point may be rejected only if it is within an exclusion period corresponding to another crossing point and the maximum or minimum corresponding to the crossing point is within an exclusion period corresponding to another maximum or minimum.

Preferably, the method may further include the step of recording the maximum or minimum value of the oscillatory signal in each measurement period.

Preferably, the step of identifying local maxima or minima that have a preselected measure indicative of the size of the maxima or minima may include determining whether the left or right side of one or more selected maxima or minima has a larger fall or rise respectively and memorising which side has the greater fall and rise and the magnitude of the largest fall or rise within a sample of the oscillatory signal and rejecting maxima or minima if the fall or rise respectively is less than a predetermined proportion of the magnitude of the largest fall or rise.

Preferably, the method may be used to detect maxima or minima of a signal representative of pulsatile blood pressure in an animal.

Preferably, the method may be used to determine a measure of the heart rate from detected maxima or minima of the signal representative of pulsatile blood pressure.

According to a third aspect of the invention, there is provided apparatus for determining the location in time of maxima and/or minima of an oscillatory waveform including sensing means to sense an oscillatory waveform and generate an oscillatory signal representative of an oscillatory waveform and a computer processing means in communication with the sensing means and having an instruction set to cause said computer processing means to perform the method as defined in any one of the preceding paragraphs.

According to a fourth aspect of the present invention, there is provided apparatus for determining the location in time of maxima and/or minima of an oscillatory waveform, the apparatus including sensing means to sense an oscillatory waveform and generate an oscillatory signal representative of an oscillatory waveform and a computer processing means in communication with the sensing means and having an instruction set to cause said computer processing means to:
  i) identify local maxima or minima that have a preselected measure indicative of the size of the maxima or minima, which exceeds a certain threshold;
  ii) compute an average interval between local maxima or minima identified in step i);
  iii) compute the duration of one or more exclusion periods dependent on said average interval;
  iv) compute a location in time of the one or more exclusion periods based on the observed signal;
  v) identify local maxima or minima in the observed signal and record identified maxima or minima except any maximum or minimum that is located in time within an exclusion period.

According to a fifth aspect of the invention, there is provided apparatus for determining the location in time of maxima and/or minima of an oscillatory waveform, the apparatus including sensing means to sense an oscillatory waveform and generate an oscillatory signal representative of an oscillatory waveform and a computer processing means in communication with the sensing means and having an instruction set to cause said computer processing means to:
  a) compute a first and a second moving average of the oscillatory signal, the first moving average having a first averaging time interval and the second moving average having a second averaging time interval longer than the first averaging time interval;
  b) compute the location in time of a plurality of crossing points, wherein a crossing point is a point of intersection between the first and second moving averages;
  c) define at least one measurement period as the interval between two crossing points; and
  d) compute the location in time of an absolute maximum or minimum of the oscillatory signal within the or each measurement period, thereby determining the location in time of each periodic maxima or minima respectively of the oscillatory signal.

According to a sixth aspect of the invention, there is provided a method of determining the frequency or wavelength of an oscillatory signal including determining the location in time of maxima and/or minima of the oscillatory signal by the method according to any one of claims 1 to 30, calculating the difference in time between maxima and/or minima and using said difference in time to calculate the frequency and/or wavelength of the signal.

Preferably, the method may be performed in real-time.

According to a seventh aspect of the invention, there is provided a method of detecting maxima and/or minima in an oscillatory signal substantially as herein described and with reference to FIGS. 1 to 12 or FIGS. 13 to 31.

According to an eighth aspect of the invention, there is provided apparatus for detecting maxima and/or minima in an oscillatory signal substantially as herein described and with reference to FIGS. 1 to 12 or FIGS. 13 to 31.

Further aspects of the present invention may become apparent from the following description given by way of example only and in reference to the accompanying drawings.

MODES FOR PERFORMING THE INVENTION

This invention provides a method and apparatus for detecting the location in time of periodic maxima or minima of an oscillatory signal. Also, the values of the maxima or minima and other parameters including peaks and troughs of the first derivative of the signal may be determined. The method may result in improved accuracy in the detection of maxima and minima over systems using constant detection thresholds, especially under conditions of rapid changes in baseline, amplitude, or frequency.

The following description is given primarily in reference to the observation and analysis of a pulsatile blood pressure waveform. However, the present invention may find application in the analysis of any periodic signal, with particular application anticipated for noisy and potentially highly variable signals such as signals obtained from biological sources and other complex and or noisy systems.

The approach according to a first preferred embodiment of the invention involves the stages of: observing a signal, high-pass filtering, and preliminary detection and parameterisation, followed by final detection. An overview of the method is presented in FIG. 1 in flow diagram form.

Figure 1:
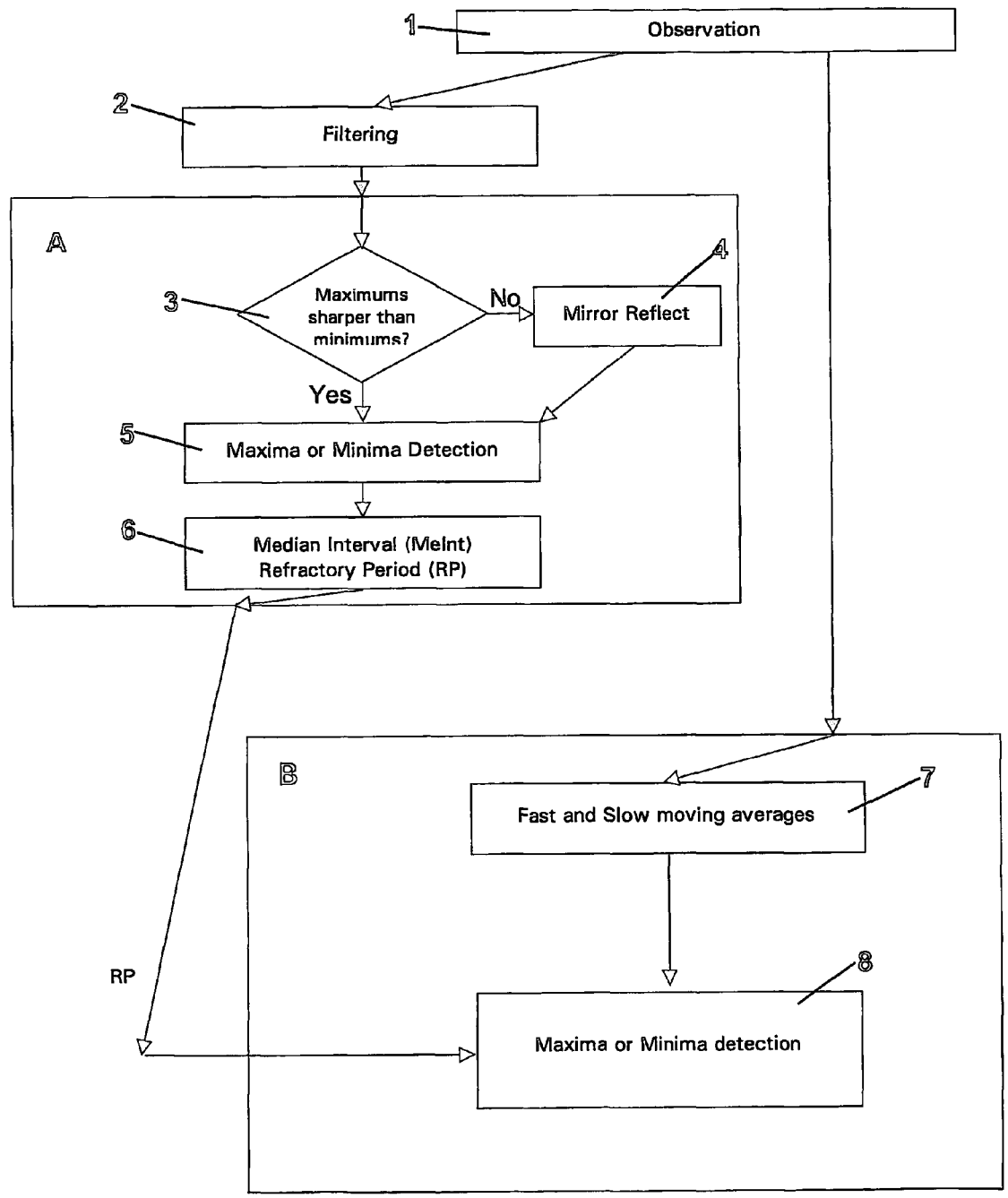
FIG. 1: shows a flow diagram of a method of signal detection and evaluation according to one embodiment of the present invention.

The first stage includes an observation step, referenced 1 in FIG. 1 and includes observation of the pulsatile signal for further analysis. Any sensor suitable for detecting the amplitude of the waveform to be analysed over time may be used. For digital analysis, the analogue signal observed may undergo analogue-to-digital conversion to produce a data array representative of the signal. A sample of the signal is then high pass-filtered in step 2 in order to reduce or remove baseline movement. If the signal has been digitised, then a digital filter is used, or alternatively, the signal may be filtered prior to digital conversion. The size of the signal sample is substantially arbitrary, but preferably is at least a few periods of the observed signal in length. For the case of arterial blood pressure detection in rabbits, a 2 second long sample period of the signal, observed with a frequency of 500 Hz was found suitable, which was then transformed through a third order high pass Bessel filter with a low cut-off frequency of 0.5 Hz. The selected cut-off frequency is selected as the level of the lowest expected frequency of the pulsatile signal, in this case 30 beats per minute (bpm) for 0.5 Hz. This is in contrast to the normal heart rate for a rabbit of approximately 200-260 bpm and therefore no significant loss of information due to including a filter is expected.

Figure 2:
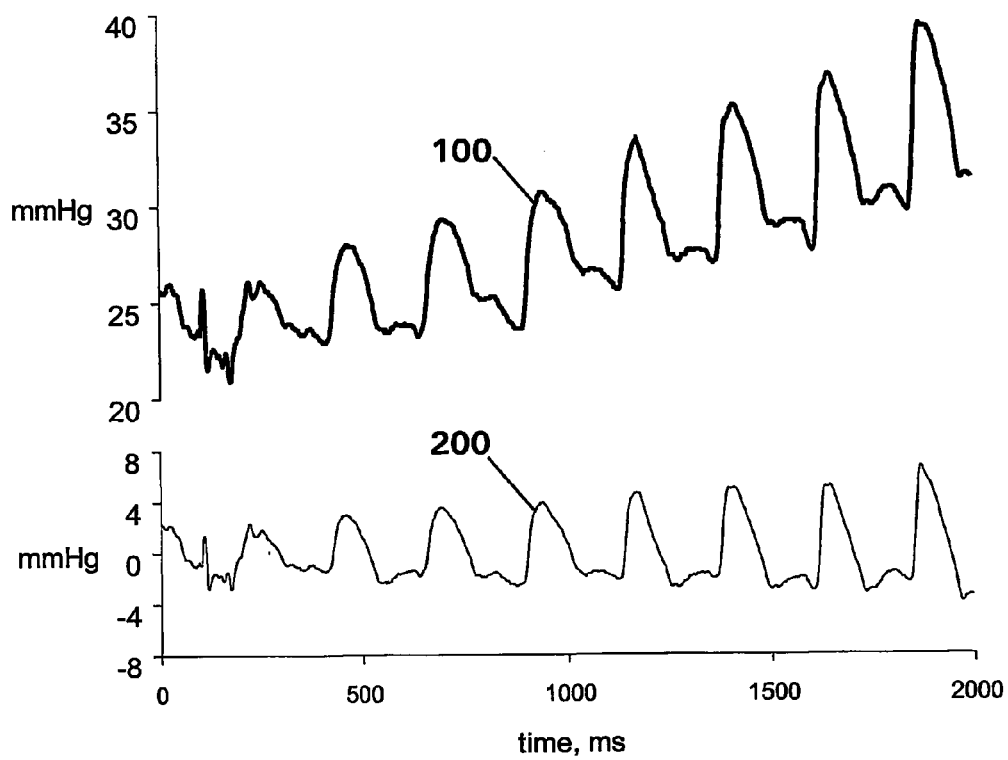
FIG. 2: shows a graph of an example of an arterial blood pressure waveform of a rabbit plotted against time and the same waveform after being high-pass filtered.

An example of an original signal 100 and a filtered signal 200 is shown in FIG. 2. The original signal 100 is an example of a possible pulsatile blood pressure signal, indicative of heart beats. The filtered signal 200 has no dc component and therefore the progressive rise in pressure in the original signal 100 does not affect the subsequent analysis of the filtered signal.

Preliminary interval detection is the next stage of the algorithm. The preliminary detection is performed on a filtered signal, and includes the steps represented within box A of FIG. 1.

Initially the sharpest of signal extremes is selected to be used as the prime detection object due to easier detection of maxima or minima having sharper signal extremes. For the case of a blood pressure signal, this is usually the maximum of the signal (or systolic peak). The sharpest extreme is determined in step 3 by comparing the difference of the maximum and average value of a sample of the signal, to the difference of the average and minimum of the same sample. If the first difference of the maximum minus average is bigger, then the sharpest extreme is a maximum and the preliminary maxima detection stage progresses to the maxima or minima detection step 5. To make this procedure less susceptible to occasional extreme deviations, approximately 0.5% of data may be discarded from both sides of the ranked data array of the sample. Other percentage values of data to be cut from the sample may be used depending on the expected signal characteristics. Also, it will be appreciated by those skilled in the art that this function may be substantially duplicated by low pass filtering the signal to remove high frequency noise, which is likely to cause many of the extreme deviations.

If the sharpest extreme is a minimum a mirror reflect step 4 is performed to mirror reflect the signal in its average through formulae (1):

$$\text{Signal}_{refl} = 2 \cdot \text{Avg}_F - \text{Signal}_{ini} \tag{1}$$

where $\text{Signal}_{refl}$ and $\text{Signal}_{ini}$ are the reflected and initial array of the signal data points respectively, $\text{Avg}_F$ is the average value of the filtered signal, and the operation is a subtraction from the doubled average of each element of the initial array. If effective filtering is used, the value of $\text{Avg}_F$ may be assumed to be zero.

Figure 3:
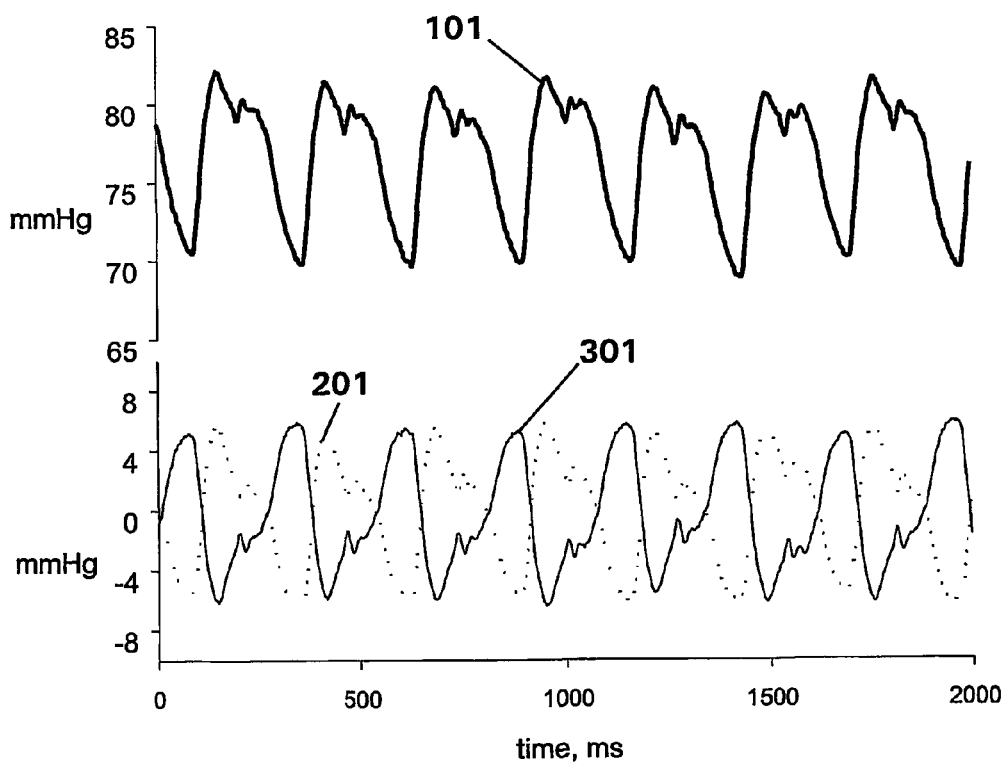
FIG. 3: shows a graph of an example of an original signal, a filtered signal and a mirror reflection of the filtered signal.

An example of a waveform signal where the minima are sharper than the maxima is presented in FIG. 3, with the original signal represented by 101, the filtered signal by 201 and the mirror reflected signal by 301. It will be appreciated by those skilled in the art that peak detection could also detect the signal minima, rather than signal maxima, in which case the signal may be reflected if the maxima are sharper. Alternatively, detection of signal maxima or minima may be dependent on the result of step 3. However, for the purposes of clarity, the following description assumes that signal maxima are being detected both for the preliminary and final detection stages.

Referring again to FIG. 1, the next step of the preliminary detection stage is a maxima detection step 5. The absolute maximum ($\text{Max}_F$) of the filtered signal sample is calculated using any appropriate algorithm, several of which are presently widely known, and an amplitude threshold value is determined by formula 2:

$$\text{Thr} = (\text{Max}_F - \text{Avg}_F) \cdot f_1 + \text{Avg}_F \tag{2}$$

where $f_1$ is a predetermined fraction selected depending on the signal characteristics. A fraction of $f_1$ equal to 0.2 was found suitable for use in analysis of rabbit pulsatile waveforms. The value of this fraction depends on the sharpness of the extremes of the particular biological signal. The sharper the extreme the larger the fraction which can be chosen. Although the absolute maximum has been found as a convenient measure of the largest oscillation, other measures may be used, such as the area under a trace formed by the signal, or extent of rise or fall to the next local maximum or minimum respectively.

In step 6, the separation in time of maxima that exceed the amplitude threshold is then determined, and the median interval between these maxima is calculated. This is performed in two stages.

In the first stage, the absolute maximum between successive intersections of the signal and the threshold (INTS) is determined. The portions of the signal between the start of the signal and the first INTS and between the last INTS and the end of signal are examined, and if there are local maxima above the threshold, the largest from each side may be added to the pool.

In the second stage, a validation process is performed by comparing the intervals between successive maxima, and rejecting the smaller of two maxima if the interval between them is shorter than some minimum interval (IntMin). A value for IntMin of 100 ms (amounting to 600 bpm) was found to be suitable for rabbit blood pressure waveforms. After the peaks have been validated, the intervals between them are assessed to determine the median interval (MeInt). In the case of no intervals being determined, the MeInt is set equal to the time length of the sample of the signal.

The median for preliminary assessment of an interval between peaks may be used, because it is independent of some extreme variation in interval distribution. However, other average values such as the arithmetic average may be alternatively used.

Figure 4:
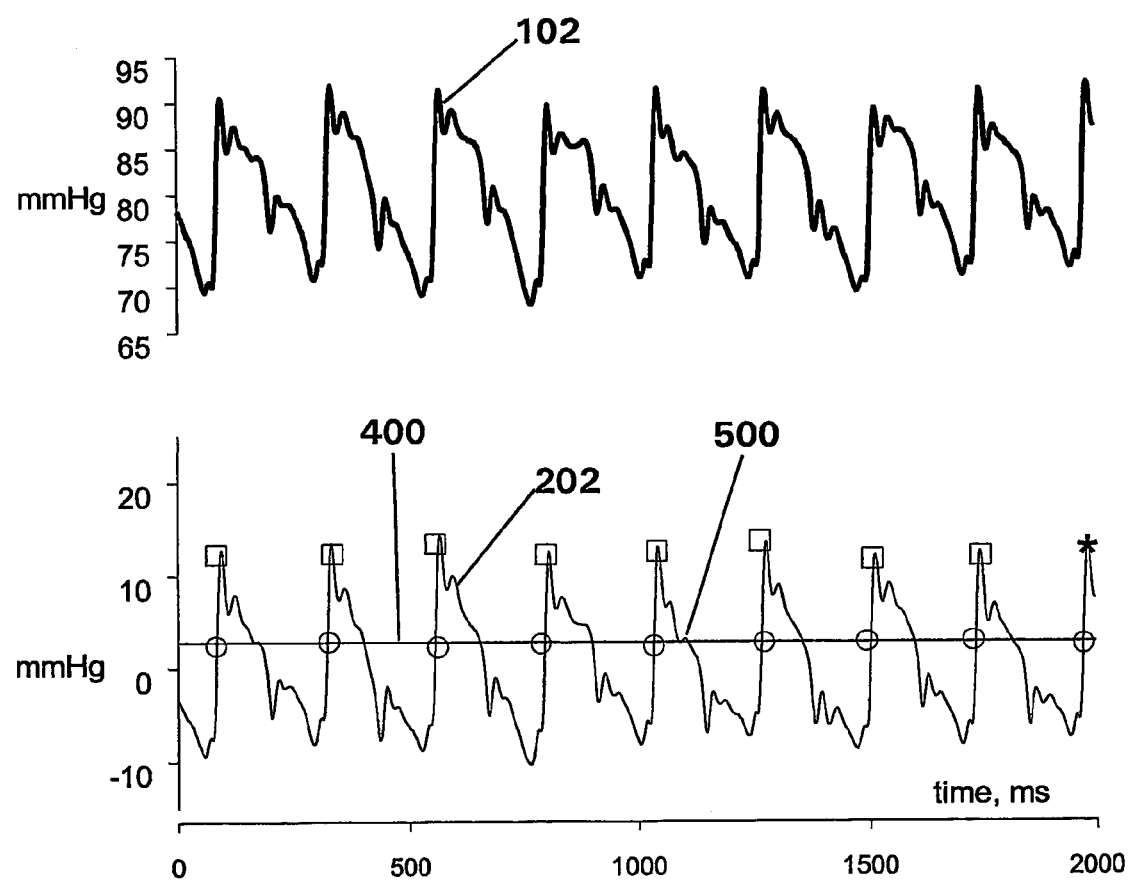
FIG. 4: shows a graph of an example of an original signal, a filtered signal and an example of a threshold for preliminary maxima detection.
Figure 5:
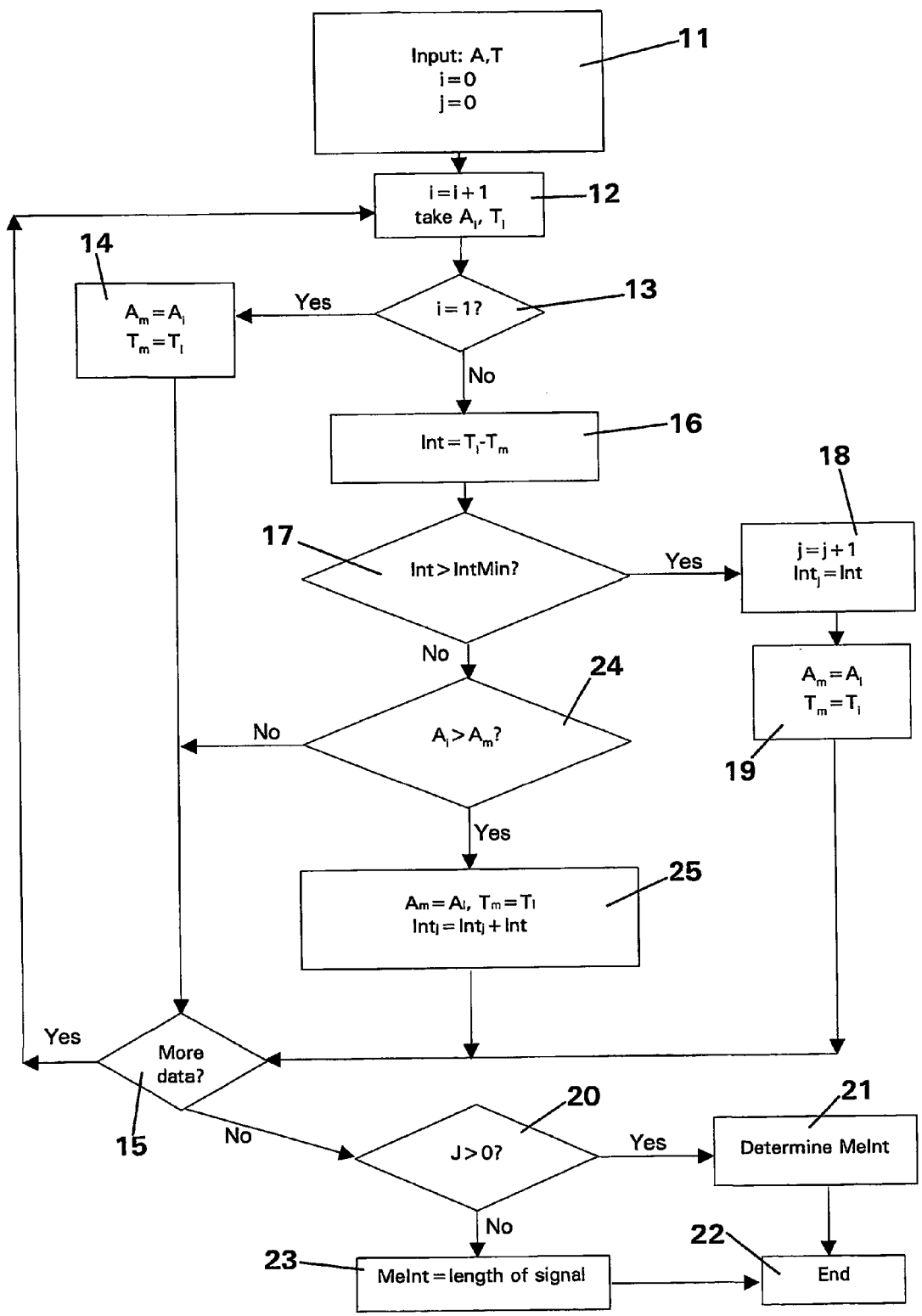
FIG. 5: shows a flow diagram of the preliminary assessment process of the intervals between successive maxima according to one aspect of the invention.
Figure 6:
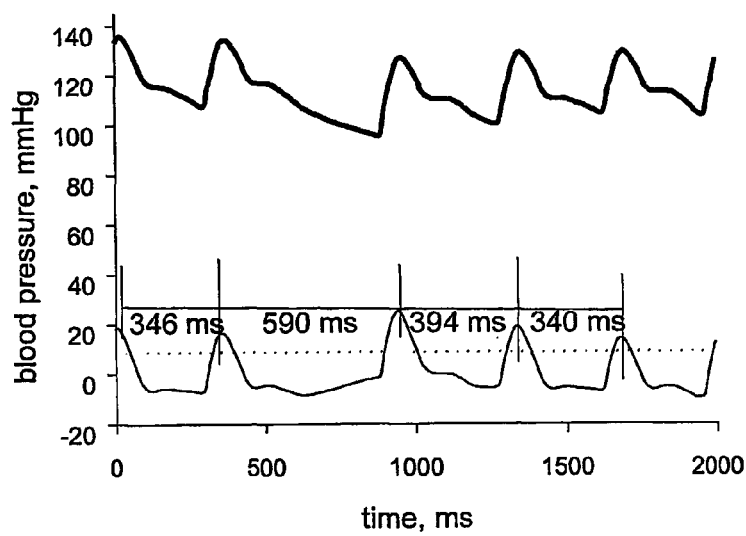
FIGS. 6 to 10: show plotted examples of the results of the preliminary detection process of the maxima of an oscillatory signal.

A plotted example of an implementation of steps 1 through 6 is shown in FIG. 4 and a suitable algorithm is presented in FIG. 5. Referring to FIG. 4, the signal 102 is an observed unfiltered pulsatile waveform, signal 202 is a filtered waveform and line 400 is the threshold. A mirror reflect step 4 was not required. Each □ in FIG. 4 represents a valid peak located between two signal to threshold intersections, which are represented by circles ○. The * represents a local maximum above the threshold which occurs after the last INTS and is recorded as a valid maximum. The local maximum 500 was rejected as an INTS due to following within 100 ms of a previous INTS.

Referring to FIG. 5, which shows the calculation steps in more detail, the first step of the process is an input step 11. Data indicative of the amplitude A and location in time T of each maximum of the filtered signal above the threshold is received, a loop counter i is set to i=0 and an interval counter j is set to j=0. In step 12, the loop counter i is incremented and a data pair of a maximum $A_i$ and corresponding time index $T_i$, is identified. The value of i is evaluated in step 13 and if i=1, the algorithm memorises the values of $A_i$ and $T_i$ as $A_m$ and $T_m$. If there is more data, then step 15 dictates that the algorithm returns to step 12, i is incremented and the next data pair ($A_i$, $T_i$) taken. This process occurs at the first iteration of the algorithm, as when only a single data pair ($A_i$, $T_i$) is present, analysis of the interval between maxima is not possible.

In step 16, the interval (Int) between the current time value $T_i$ and the memorised time value $T_m$ is determined and in step 17 this difference is compared with the minimum set time interval, IntMin. In the case that Int>IntMin, then the maximum is deemed valid, the algorithm proceeds to step 18, the interval counter j is incremented and the value of Int is stored as $Int_j$. In step 19, the current data pair is memorised; $A_m=A_i$ and $T_m=T_i$, replacing the existing values of $A_m$ and $T_m$. If there are more data pairs ($A_i$, $T_i$), step 15 causes the process to repeat the cycle commencing with step 12.

In the case that Int<IntMin in step 17, the process proceeds to step 24. The greater of $A_i$ and the memorised $A_m$ is determined. If the current maximum value $A_i$ is greater, then this value replaces the existing value of $A_m$ and the corresponding time value $T_i$ replaces the existing $T_m$, thus rejecting the previous memorised data pair in preference for the current pair. The value of the interval between the current and previous valid peak is then calculated as $Int_j=Int_j+Int$. The algorithm repeats if there is more data pairs ($A_i$, $T_i$), and otherwise proceeds to step 20.

In step 20, the process involves evaluating whether any interval between two maxima has been determined by evaluating whether j>0. If j is greater than zero, then the median interval (MeInt) is calculated in step 21 and the algorithm ends at step 22. If j=0, then the median interval is set to the length of the sample of the signal and the algorithm ends at step 22.

Figure 7:
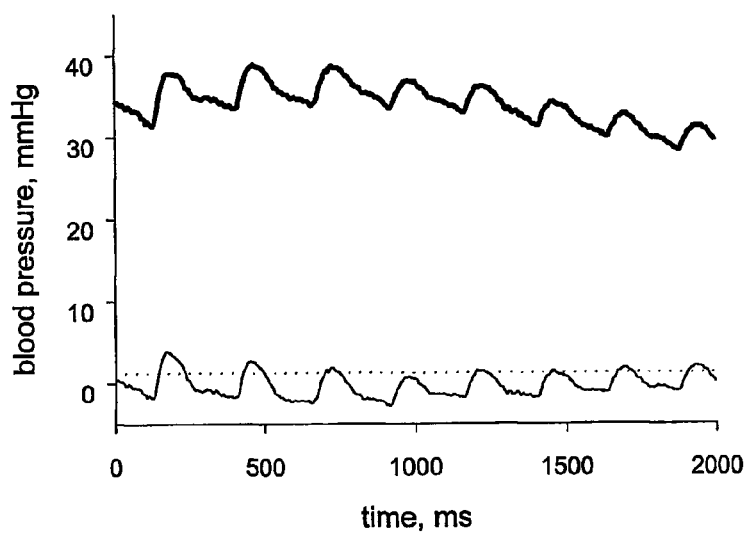
Figure 8:
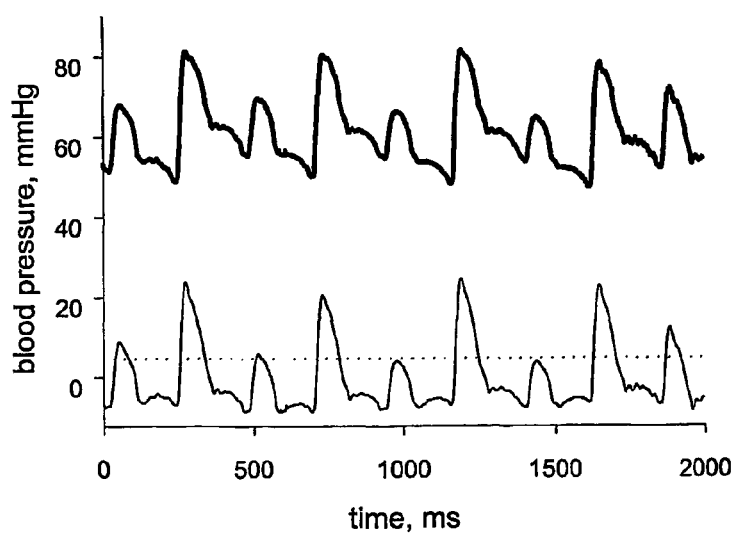
Figure 9:
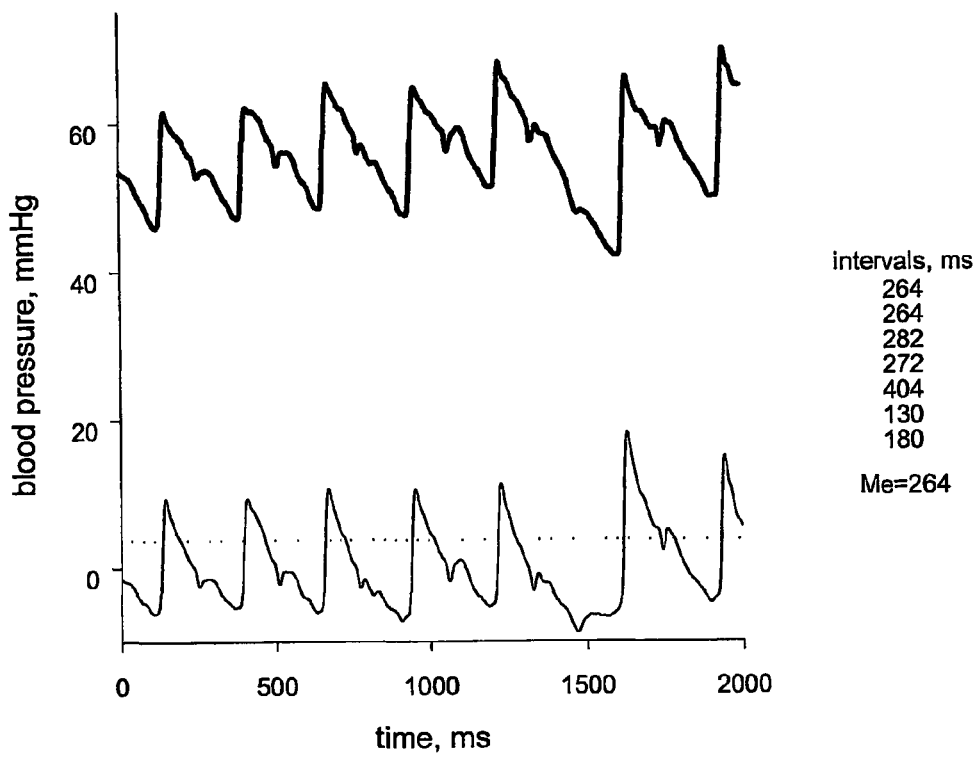
Figure 10:
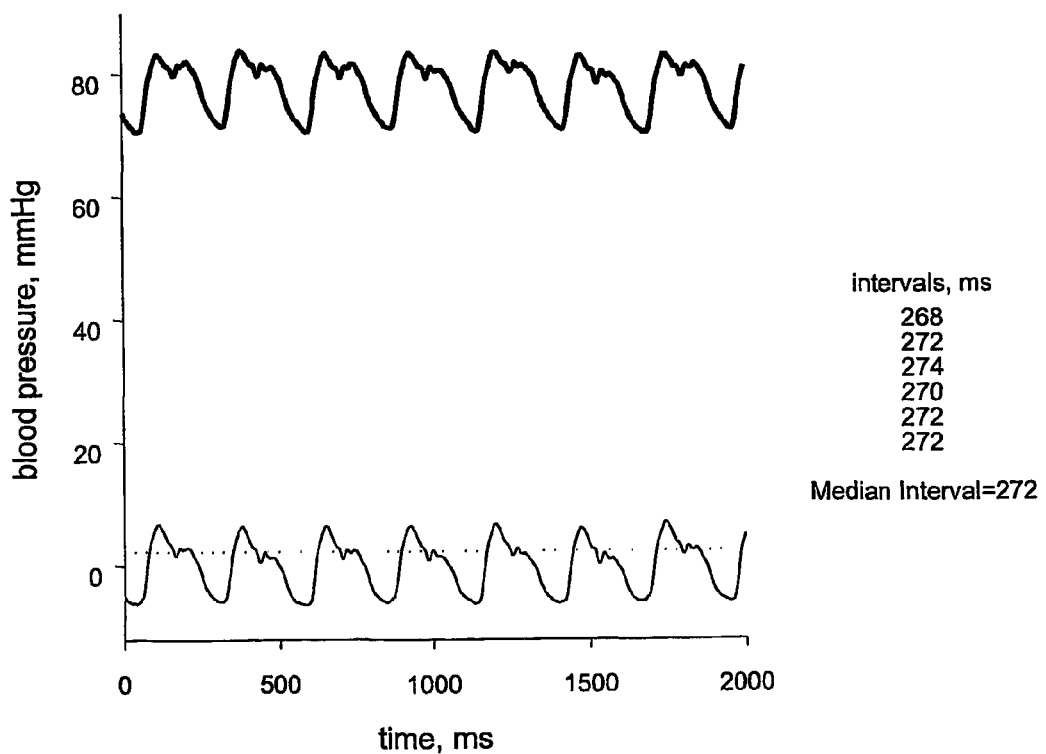

Plotted examples of the results of the preliminary interval assessment are shown in FIGS. 6-10. An example of a usual case for blood pressure waveforms is presented in FIG. 6. There are 5 maxima above threshold, and one unfinished maximum at the end of the signal, which is not taken into account. The median of four intervals serves as a good estimate of the interval. FIGS. 7 and 8 represent cases where some peaks are below the threshold, but a median value still represents the intervals properly. FIG. 9 represents a case where a big notch is determined as an extra peak, but again the median is a correct measure of interval. FIG. 10 represents a case where a noisy signal causes a large amount of extra peaks to be determined after the first step of detection, but then by rejecting intervals smaller than IntMin, the right assessment of an interval is obtained.

Referring again to FIG. 1, once the median interval MeInt has been determined, the refractory period (RP) as a fraction of MeInt is calculated. The fraction is chosen from experience and a suitable value has been found to be 0.7, although this may be varied depending on the signal characteristics. This is discussed in more detail herein below in relation to the second embodiment. Next, final detection, represented by the steps within box B may be completed. Final detection includes of the analysis of the original signal by producing two moving averages in step 7. A fast and a slow moving average is calculated, with a shorter and longer averaging time interval respectively. Any appropriate average may be used such as the arithmetic mean or median value for the moving averages.

Figure 11:
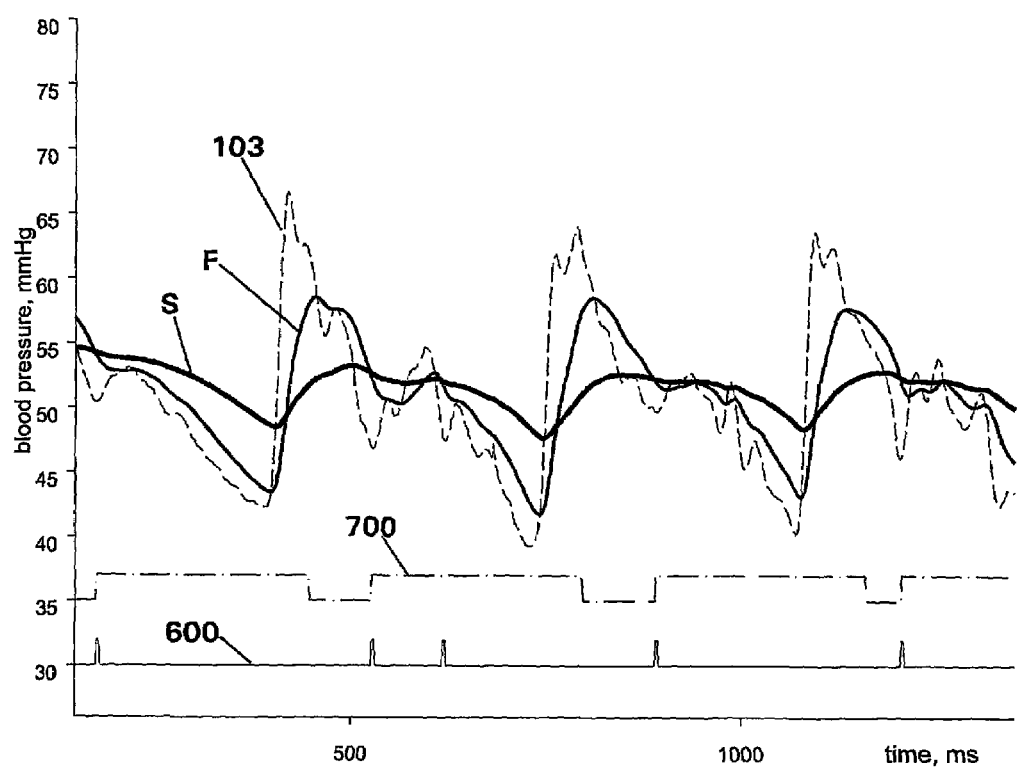
FIG. 11: shows a graph of an example of an oscillatory signal, a slow and fast moving average of the oscillatory signal and the periodic onset of an exclusion period.

Using moving averages provides a means of detection independent of baseline movement as well as allowing for noise in the signal to be ignored. Analysing the moving averages on a point-by-point basis in step 8, the point where the fast moving average F of the original signal 103 first becomes smaller than the slow moving average S (see FIG. 11) is determined as an after peak crossing point (APCP). Each detection of an APCP is indicated by a spike in plot 600. A maxima, which is the maximum value between two successive APCP, is determined as valid only if the last APCP comes after a predetermined refractory period (RP) since the previous APCP has elapsed. The onset of the RP is indicated by the raised portion of plot 700. FIG. 11 shows an example of detection with some maxima between APCP being rejecting as occurring within the RP.

Throughout the remainder of this description, the term refractory period or RP will be used in specific reference to the analysis of blood pressure signals. However, persons skilled in the art will immediately recognise that any suitable exclusion period may be applied to other signals in a like manner as the refractory period is applied to blood pressure signals.

Figure 12:
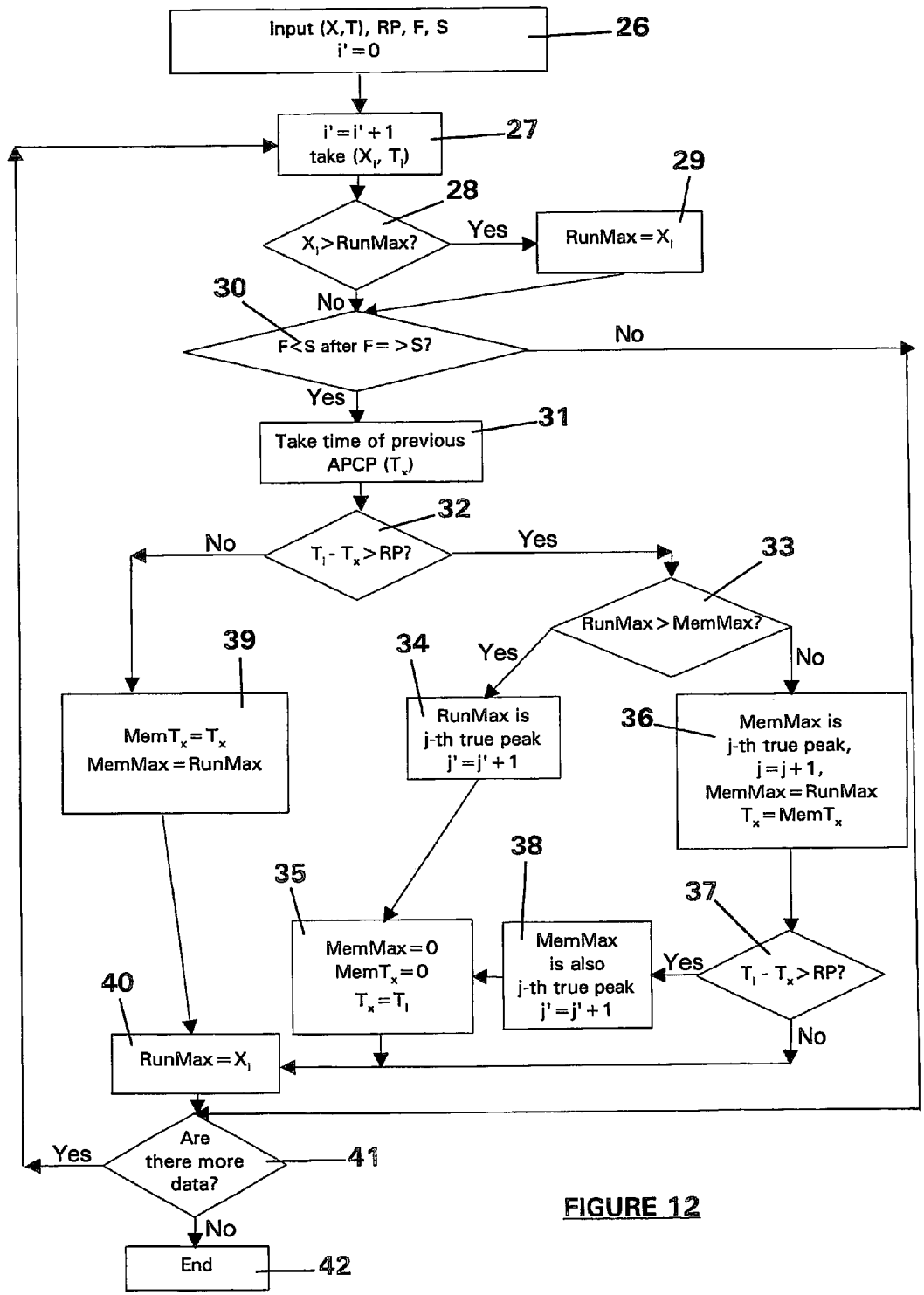
FIG. 12: shows a flow diagram of the process of final assessment of the intervals between successive maxima according to one aspect of the invention.

A flow diagram showing the process for final maxima detection in detail is given in FIG. 12.

The process starts at step 26, the original signal has been observed in step 1 (see FIG. 1) to produce a data set of amplitude values X and times T associated with the values X, producing a set of data pairs (X,T). The refractory period RP, fast moving average F, and slow moving average S, are also calculated for use as input variables to the final detection process. A loop counter i is set to i=0.

In step 27, a loop counter i' is incremented and a data pair $(X_i, T_i)$ is taken for analysis. If the current value of $X_i$ is greater than a stored maximum RunMax (initially null, zero or other appropriate value) of previous values X, then the current value $X_i$ is stored as RunMax, thus keeping a monitor of the maximum value. Step 30 involves monitoring the values of F and S, with the process cycling through steps 27, 28, optionally 29, 30 and 41 until the fast moving average first becomes less than the slow moving average. Once F becomes less than S, steps 31 and 32 involve computing the time interval between the previous APCP, which has a corresponding time $T_x$ (initially zero) with the current APCP, with corresponding time $T_i$.

If the time interval between the successive APCP is greater than the value of RP, the value of RunMax is compared with a value MemMax, which is initially null, zero or other appropriate value. If RunMax is greater than MemMax, then RunMax is a true maximum and is memorised in step 34 and an interval counter j' is incremented. In step 35, the stored values of MemMax and MemT$_x$ are set to zero and $T_x$ set to time $T_i$. In step 40, RunMax is set to the value of X corresponding to the time $T_i$ of the current APCP and the process iterates (step 41) if there is more data to analyse and otherwise ends at step 42.

If the current APCP falls within the RP, as determined in step 32, the value of RunMax and the time of the previous APCP (the current $T_x$) are memorised, with RunMax stored as MemMax and $T_x$ stored as MemT$_x$. If there is more data, the process iterates through steps 27-30 as described herein above until the next APCP. If there are two APCP within RP, the later one only is memorised.

At the next APCP, if the corresponding time is outside the RP, the value of the last maximum prior to the current APCP and after the previous APCP is compared with the value of MemMax. MemMax≠0 if a previous maximum was within the RP. If RunMax<MemMax, or alternatively if MemMax is within a certain predetermined percentage, say 90% of Runmax, then the maximum associated with MemMax is determined as a true peak and is memorised together with its corresponding time value $T_x$, which was stored as MemT$_x$. The interval counter j' is incremented, RP recalculated based on the APCP associated with MemMax, the current value of RunMax is memorised as MemMax for comparison with the next maximum and MemT$_x$ is memorised as $T_x$ as this is now the time of the last valid maximum.

It is now possible to evaluate whether the current maximum is within the RP of the previous maximum, which has just been determined in step 36 to be a true or valid maximum. If it is outside the RP, then the current maximum, which has been stored as MemMax in step 36 is also a true maximum and thus is memorised, the interval counter incremented, MemMax and MemT$_x$ reset to zero and $T_x$ set to the time corresponding to the current peak, $T_i$ (see steps 38 and 35). If the current maximum is within the RP, the value is stored as RunMax, waiting the next peak after which time the process repeats.

Thus, if the frequency of the waveform being monitored increases, it becomes more likely that a maximum will fall within the RP associated with a previous APCP and corresponding maximum. However, when the next sample of signals is analysed, the MeInt will shorten and thus the RP will be shortened further if required.

The foregoing description has been given in relation to blood pressure waveforms. However, as stated previously, the present invention may find application to many different waveforms. Due to the characteristics of the blood pressure waveform, a secondary local maxima, for example a pulse wave reflection or dichrotic notch tends to follow the primary local maximum (the systolic peak) of the waveform. As this second maxima does not indicate a new heart beat, it must be disregarded. Therefore, an exclusion period, referred to as a refractory period (RP) in specific reference to blood pressure signals is located in time directly following the after peak crossing point. This location helps ensure that the second maxima falls within the refractory period. Alternatively, the RP may be located in time preceding a systolic peak with substantially the same effect.

For other waveforms, the location of an expected secondary local maximum in each period may be different. For example, in a system where reflections of the signal cause a secondary maximum to occur closer to the next primary maximum, the exclusion period may be defined relative to the next primary maximum. The exclusion period associated with an APCP may be in an entirely different period, for example if the reflected wave does not reach the observation point until after one or more periods of the waveform have elapsed. If the exclusion period is located remote from the APCP between two times t1 and t2 defined relative to the APCP, step 32 in FIG. 12 still tests whether an APCP falls within this period, but the test would be: $t1 < T_i < t2$?

Figure 13:
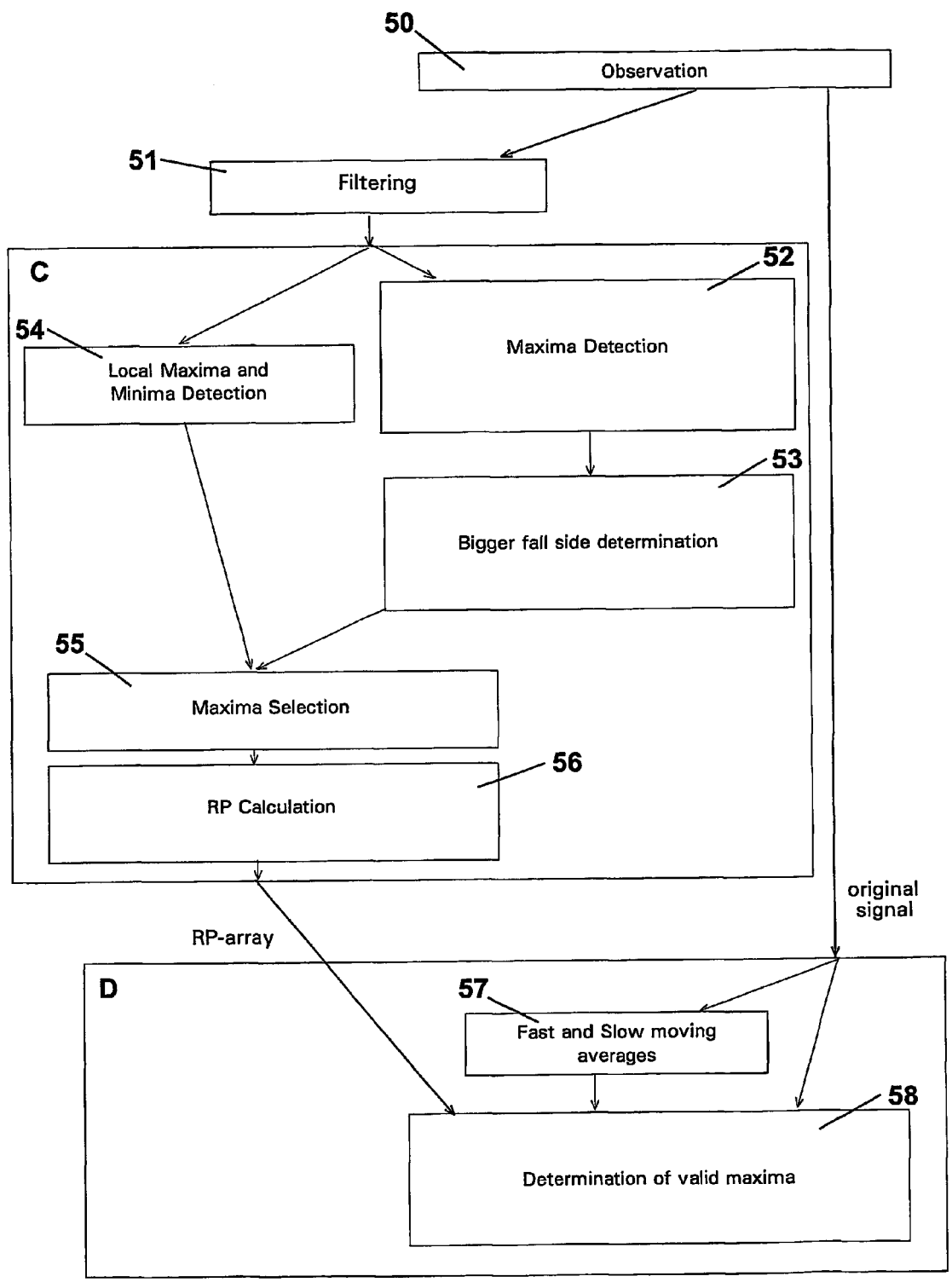
FIG. 13: shows a flow diagram of a method of signal detection and evaluation according to a second embodiment of the present invention.

The approach according to a second preferred embodiment of the invention also involves stages of observation, filtering, preliminary detection and parameterisation, and final detection. However, the preliminary detection and parameterisation stage is accomplished using a different method and the signal is band-pass filtered prior to preliminary detection, rather than high pass filtered. Further, the final detection process is different, involving two refractory periods and utilising a different measurement period. A flow diagram of the overall process according to the second embodiment is shown in FIG. 13 and the following description highlights the differences between the second and first embodiments.

After the blood pressure waveform to be analysed has been observed in step 50 using a suitable sensor, it is band-pass filtered in step 51 in order to eliminate baseline movement and high frequency noise. A third order Bessel high-pass filter having a 0.5 Hz cut off and a third order Bessel low-pass filter having a 15 Hz cut off frequency has been found suitable for a blood pressure waveform from a rabbit. Generally, a low pass filter with a minimum cut-off frequency of approximately 0.1 Hz is preferable to obtain a signal reasonably centred around zero and a high cut off frequency sufficiently low to smooth most of the irrelevant waveform noise, but high enough not to distort the proportions of the waveform. The lower boundary for the high cut off may be chosen above the highest frequency of the oscillations which are expected to be possible. For example, for a rabbit this would be expected to be approximately 10 Hz (600 beats per minute). However, the selected cut off frequencies are not critical for the detection. It has been found that the algorithm is quite stable under a wide range of the parameters.

Preliminary interval detection is then performed on the filtered signal in steps 52-56 and is performed in three parts. These three parts include the steps contained within box C in FIG. 13.

Figure 14:
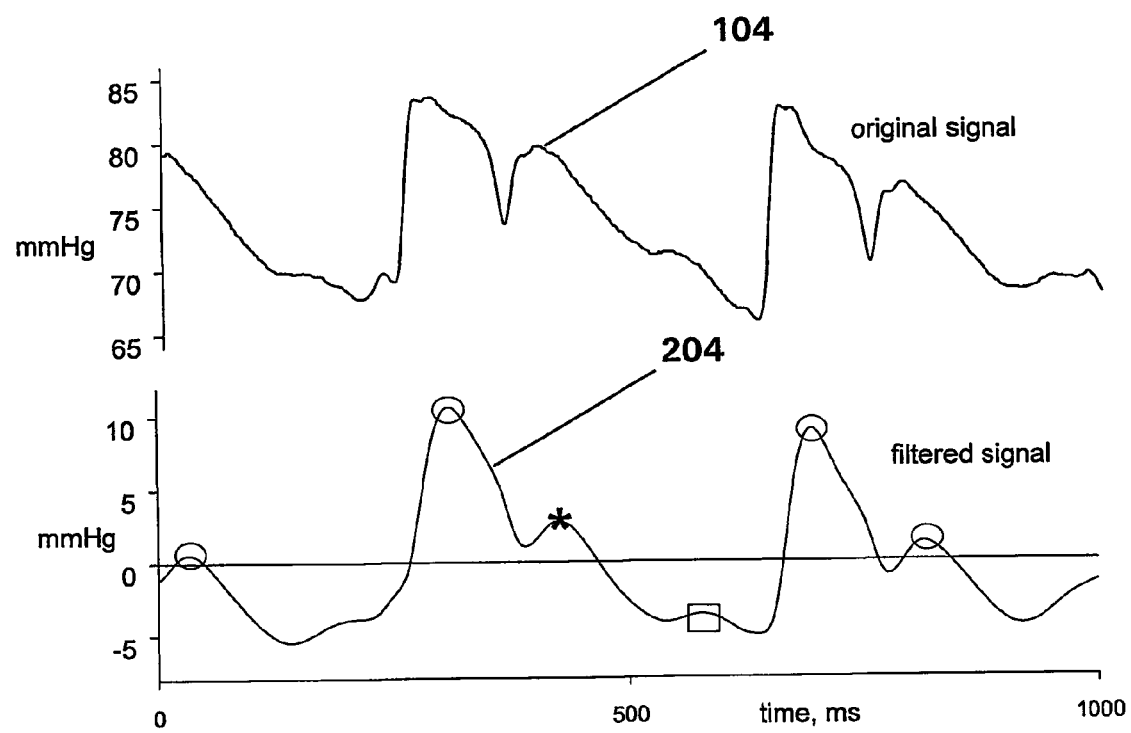
FIG. 14: shows a plot of an original and a filtered signal evaluated against a threshold.

During the first part, identification of the bigger vertical fall side of the maxima is performed in steps 52 and 53. Clusters of data associated with absolute maxima in the areas above the zero-line of the filtered signal are identified in step 52. In FIG. 14, which shows a plot of an original signal 104 and filtered signal 204, the absolute maxima (AbsMax), which are taken into account are shown by circles ○ in the filtered signal 204. The local maximum * in the area above zero-line and the maximum in the area below zero-line are shown. These are disregarded. For each □ AbsMax, the nearest left and right local minimum (LocMinleft and LocMinright), nearest the left and right absolute minimum in areas below zero-line (AbsMinleft and AbsMinright) are determined, and the left vertical fall (VFleft) and right vertical falls (VFright) are calculated by formulae (3, 4):

$$VF_{left} = AbsMax - LocMin_{left} \quad (3)$$

$$VF_{right} = AbsMax - LocMin_{right} \quad (4)$$

Figure 15:
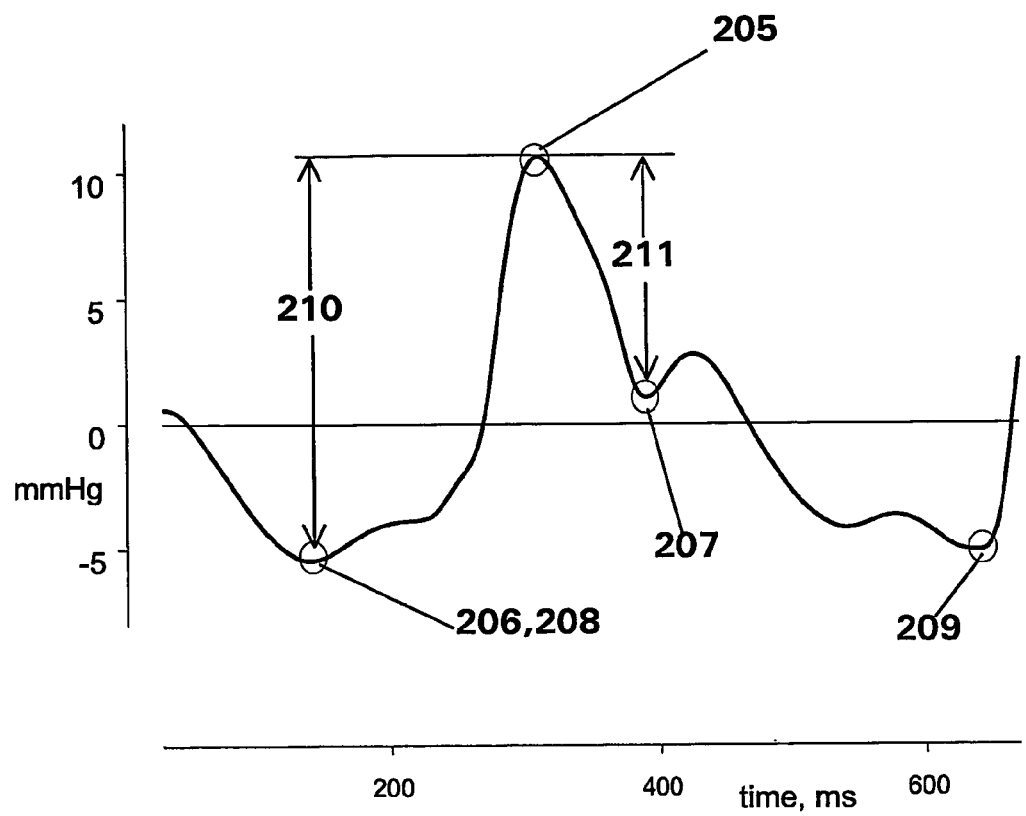
FIG. 15: shows a graphical example of the determination of the larger fall side of a maximum.
Figure 16:
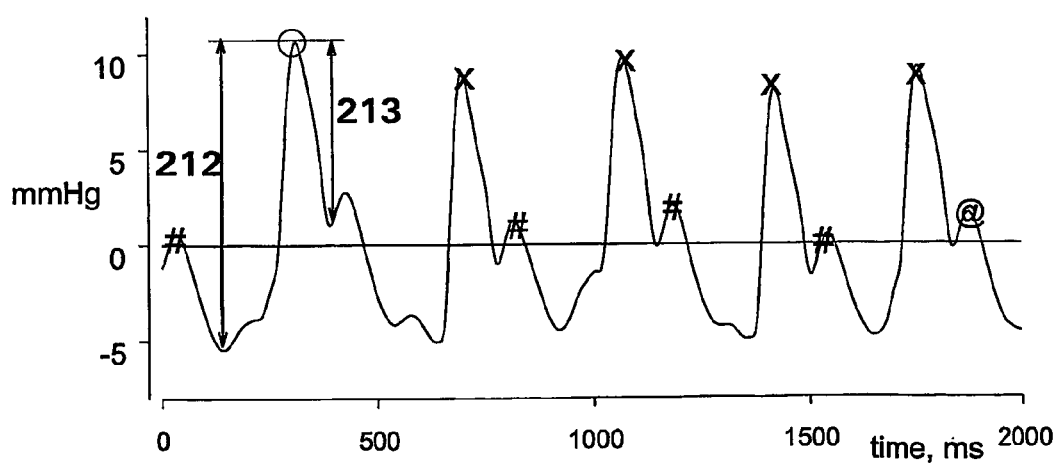
FIG. 16: shows a graphical example of the selection process for maxima which exceed a threshold.

An example of the determination of an AbsMax 205, LocMinleft 206 and LocMinright 207, AbsMinleft 208 and AbsMinright 209, and VFleft 210 and Vfright 211 calculation is shown in FIG. 15. The LocMinleft 206 and AbsMinleft 208 coincide in the waveform shown in FIG. 15. In step 53, an example of an implementation of which is shown in FIG. 16, 50% of the biggest by AbsMax maxima are selected from the sample, with the others, marked with a # in FIG. 16 rejected. From the selected largest maxima, the next selection is performed—only peaks, which have at least one of the absolute minima not the same as its local minimum are selected. Thus, only the first maxima, marked with a ○ is retained, the maxima marked with an X rejected. The aim of this selection is choosing peaks with a definite notch. If no such peaks is determined yet, any peak is used. The maximum marked with an @ is considered with the next sample. The VFleft and VFright of the waveform in FIG. 16 are referenced by 212 and 213 respectively.

Next, the fall difference (FD) is calculated for each peak using equation 5:

$$FD = VF_{left} - VF_{right} \quad (5)$$

The side of the bigger vertical fall is redetected after each sample by the sum of a predetermined number of previous selected peak fall differences. The use of approximately fourteen previous fall differences has been found suitable for the purposes of this invention, although other numbers may be used. If the FD is positive the side of bigger fall is the left, if negative the right.

Figure 17:
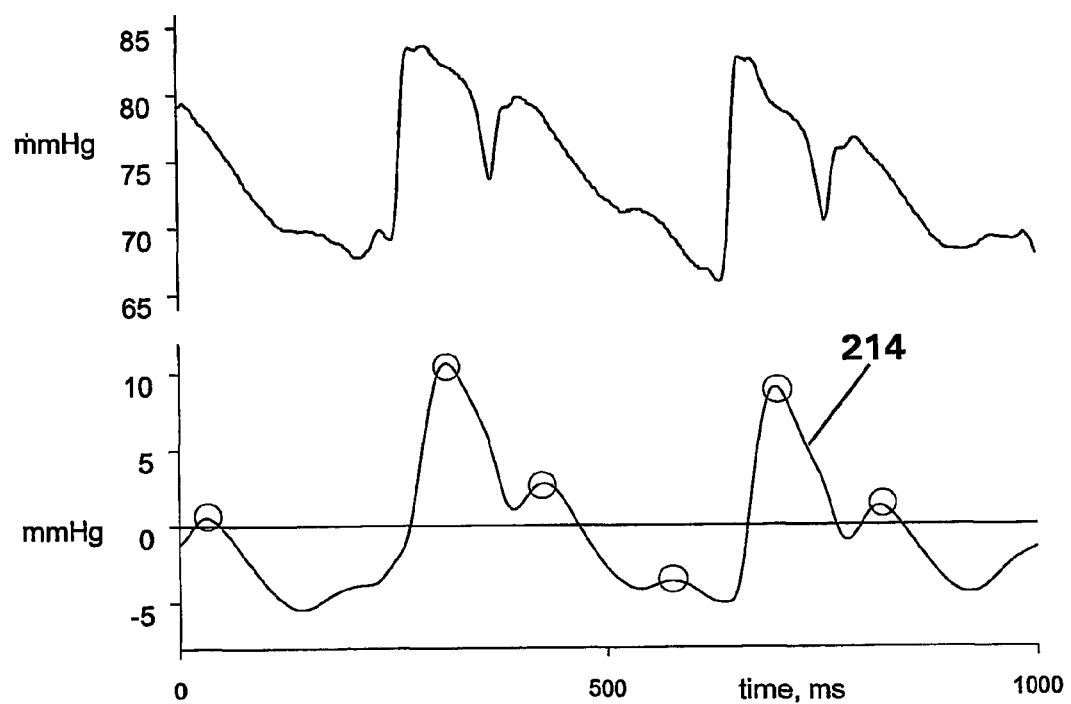
FIG. 17: shows a graphical example of the determination of local adjacent maxima.
Figure 18:
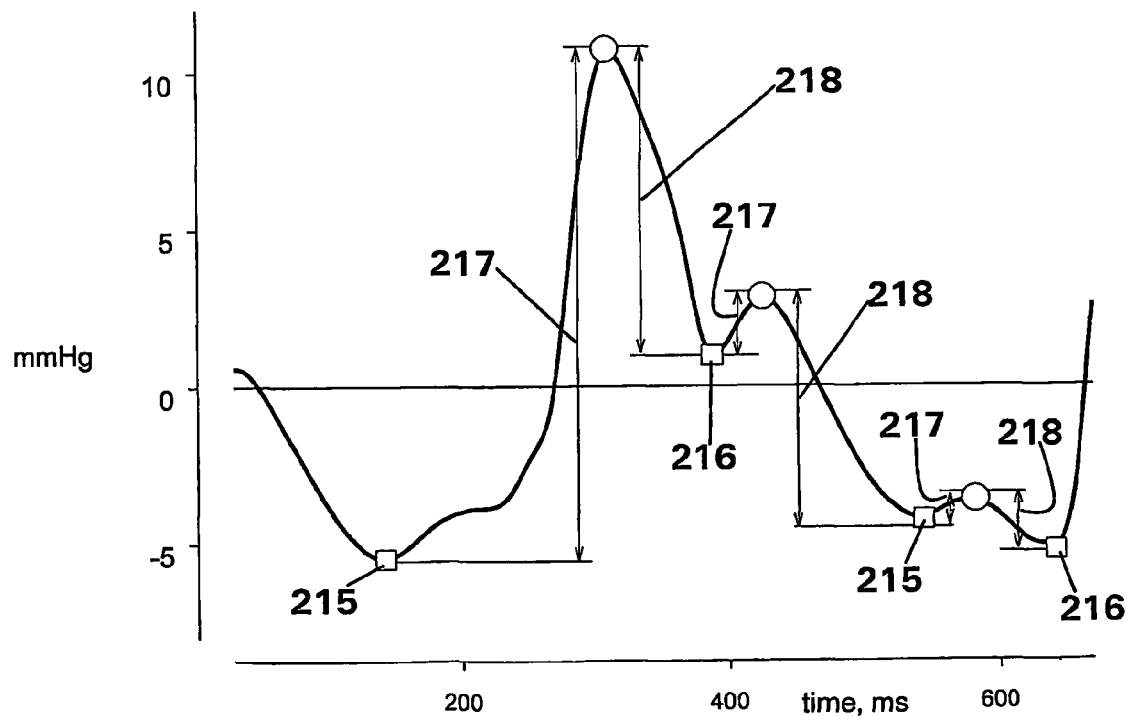
FIG. 18: shows a more detailed graphical example of the determination of local adjacent maxima.

During the second part, which includes steps 54 and 55, all maxima in a sample are compared by the value of the bigger vertical fall. For this purpose the clusters of data associated with all local maxima are identified. Local maxima (LocMax) of the sample of the filtered signal 214 are shown in FIGS. 17 and 18 as circles ○. For each local maximum, the nearest left local minimum 215 and nearest right local minimum 216 are determined (see FIG. 18). Also, the left and right vertical falls, referenced 217 and 218 respectively, are calculated. The vertical falls of the bigger side (determined at the previous step) are taken for the selection of maxima in the filtered signal for use. The selected maxima are those which have a vertical fall within a predetermined percentage of the maximal fall in the sample. A selection criterion of 35% of the maximal fall in the sample has been found suitable, although this may be varied depending on the characteristics of the signal. The use of the bigger side for selection puts the notch in a disadvantage against the true peak, because the bigger side for the true peak is the smaller side of the notch.

During the third part, which includes step 56 in FIG. 13, an array of Refractory Period (RP) values is formed. The time intervals between successive selected maxima in step 55 are determined. An interval estimate is then calculated after each determined interval and that value is retained until the next interval is determined. To calculate the value of the Interval Estimate at a specific time, an average of a predetermined number of prior intervals is taken. For example, the Interval Estimate may be the third lowest term in an ordered sequence by magnitude of the last seven intervals. Other averages may be used, for example the median value or the arithmetic mean.

Figure 20:
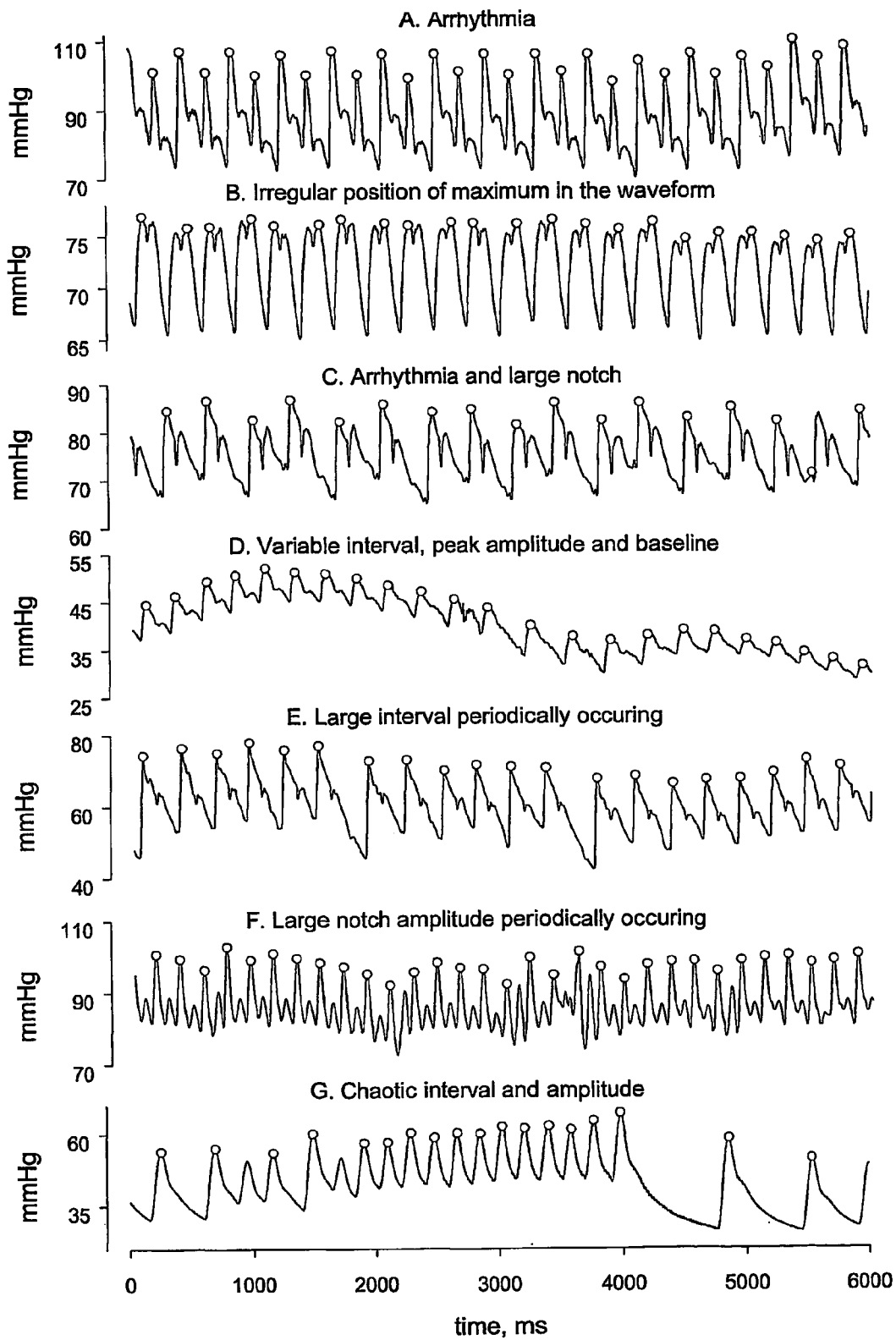
FIG. 20: shows examples of possible pulsatile waveforms.

In parallel to the interval estimate (IE) an array of refractory period (RP) values, calculated as a fraction of IE is determined. A fraction equal to 0.7 and RP limited to a minimum value of 100 ms, which is a conservative assessment of the minimal interval possible for rabbit (related to the heart rate of 600 beat per minute) were used. These values may be varied depending on the expected signal characteristics. In some cases, where there is a large, random variation in the intervals between maxima and maxima amplitude, a lower fraction of IE for the calculation of RP is used, for example 0.4. An example of such a signal is shown in FIG. 20G. The fraction is chosen based on experience.

Figure 19:
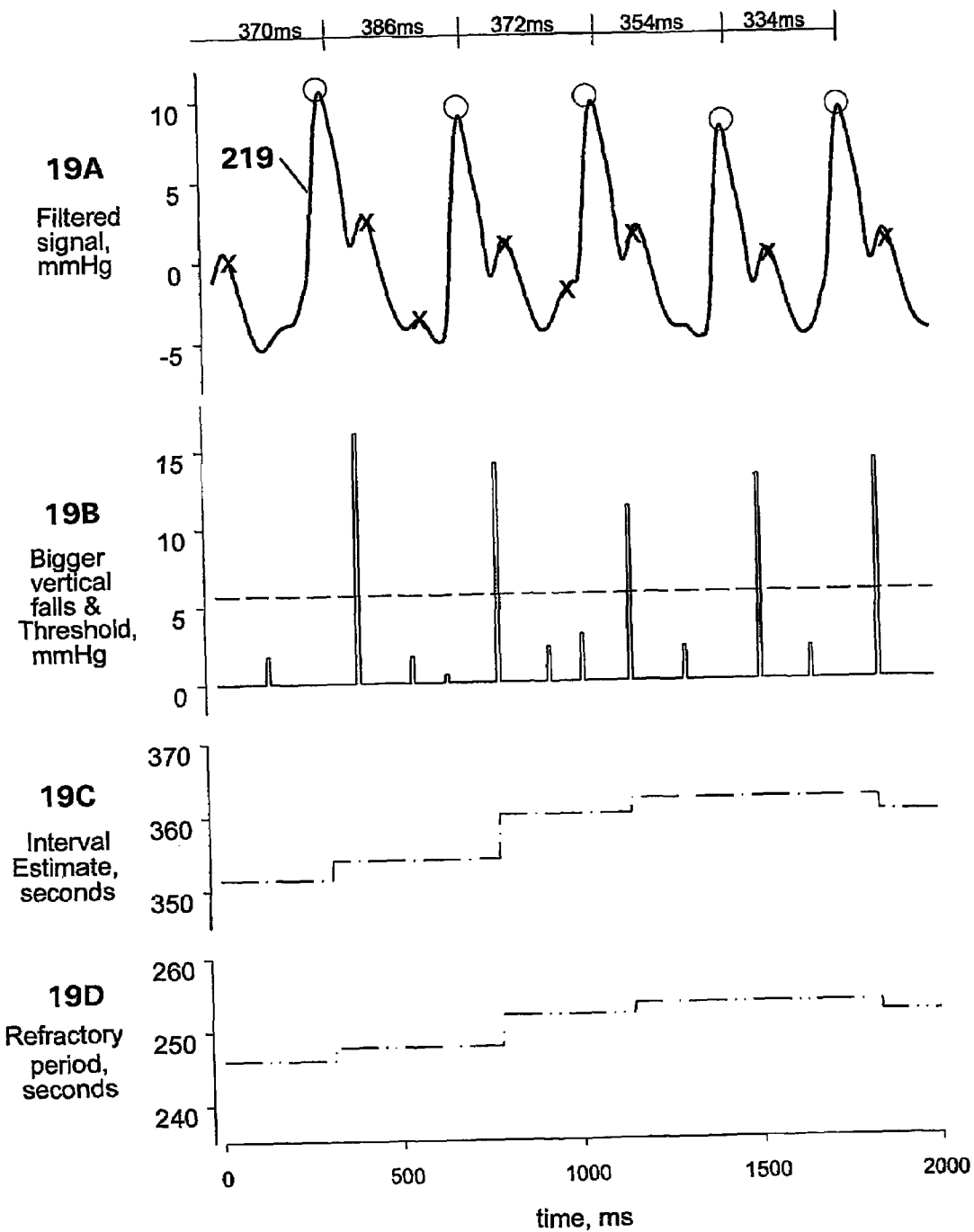
FIGS. 19A-D: shows a graphical example of the analysis of a filtered signal to compute a refractory period.

An example of the calculation of RP in relation to a filtered signal 219 is shown graphically in FIG. 19. The local maxima selected in step 55 are marked with a circle ○ and the rejected local maxima marked with a cross X in FIG. 19A. The value of the vertical falls is shown by a spike at the moment in time of the right local minimum in FIG. 19B. The threshold for detection is indicated by the dashed line in FIG. 19B.

FIG. 19C shows a plot of the interval estimate over time and FIG. 19D shows the corresponding RP. The actual intervals between selected peaks are shown at the top of FIG. 19. As described herein above, only maxima with a vertical fall greater than the threshold are used for the calculation of the interval estimate and refractory period.

Figure 21:
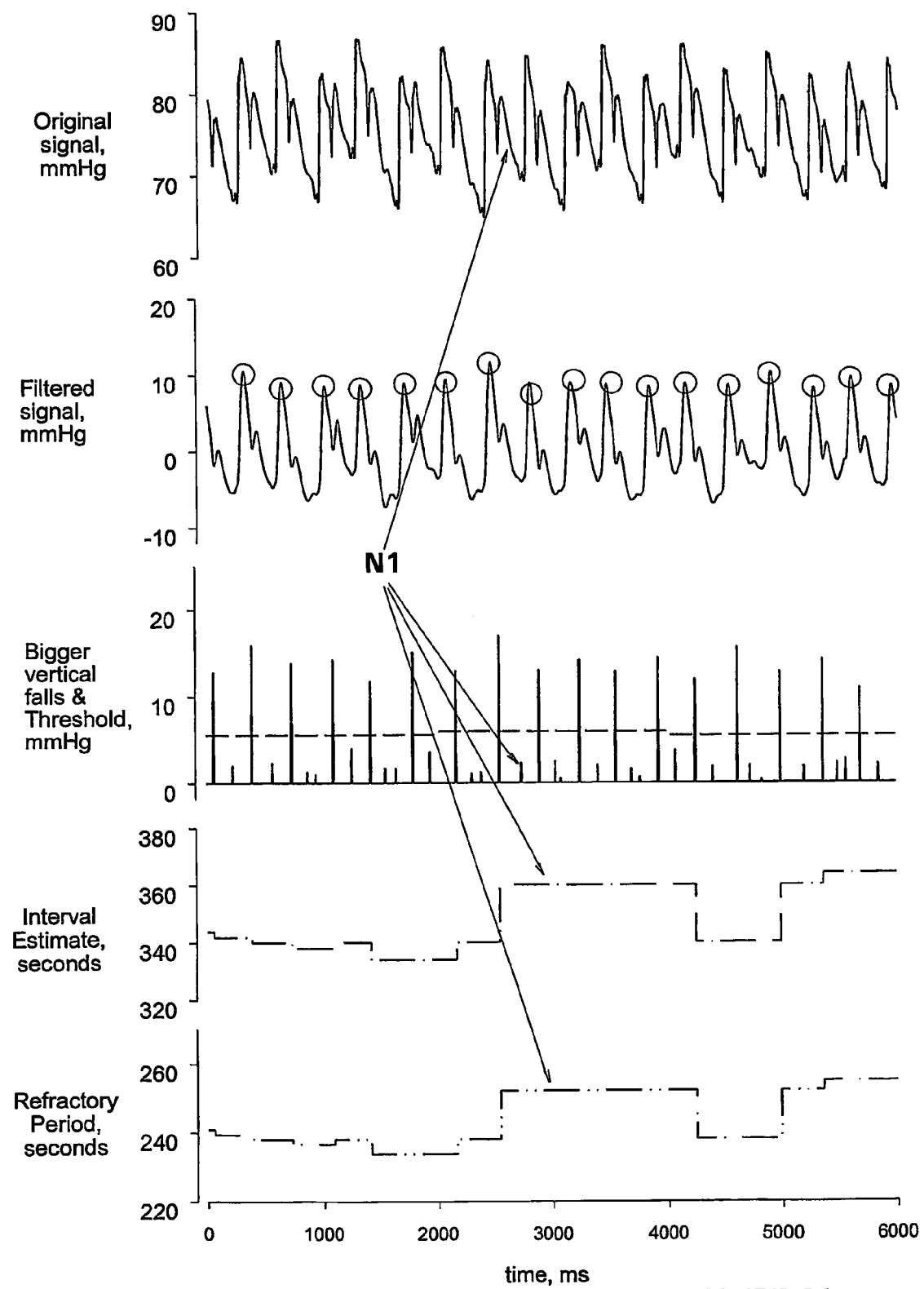
FIGS. 21-23: show graphical examples of the analysis of a filtered signal including large notches.
Figure 22:
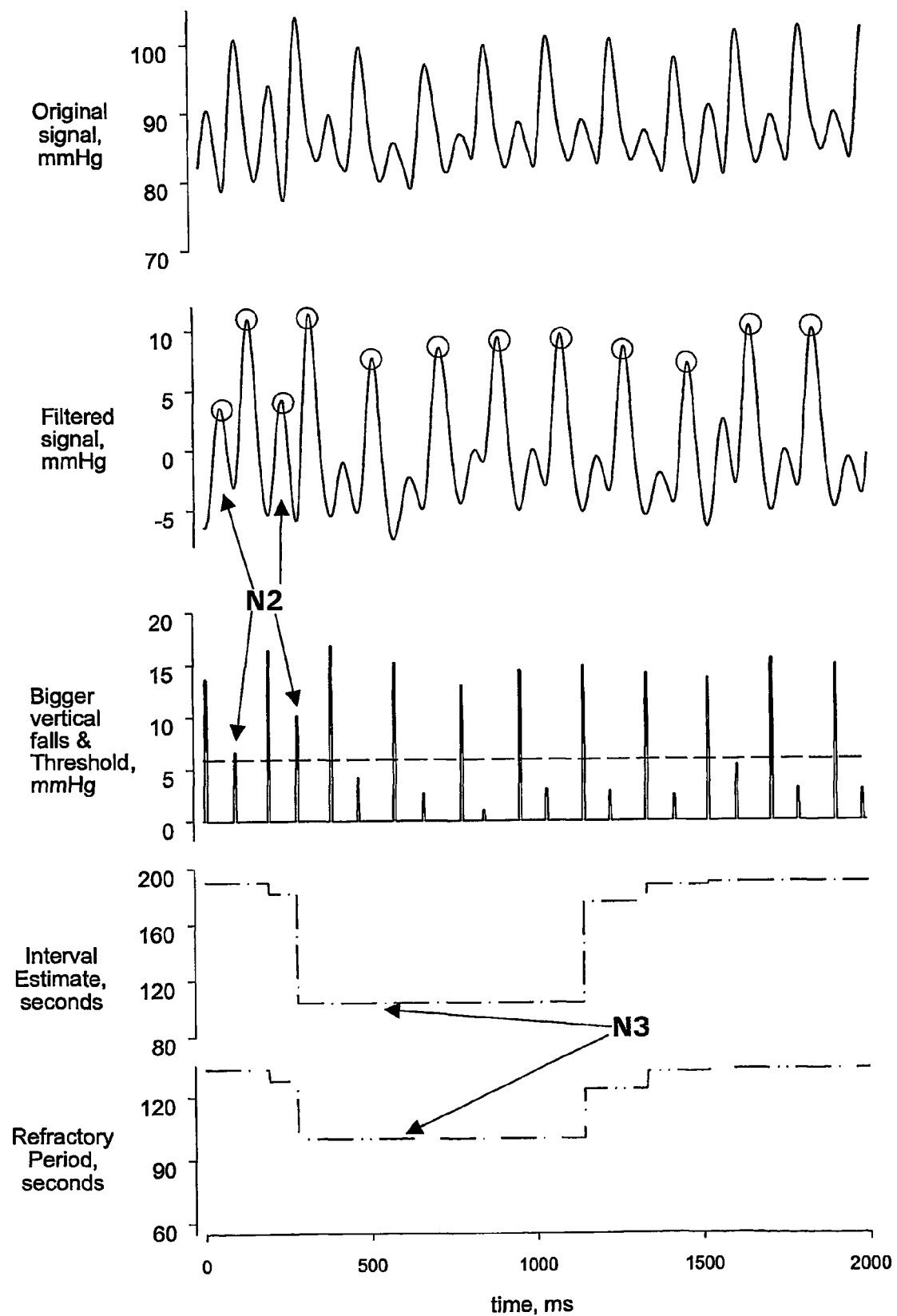
Figure 23:
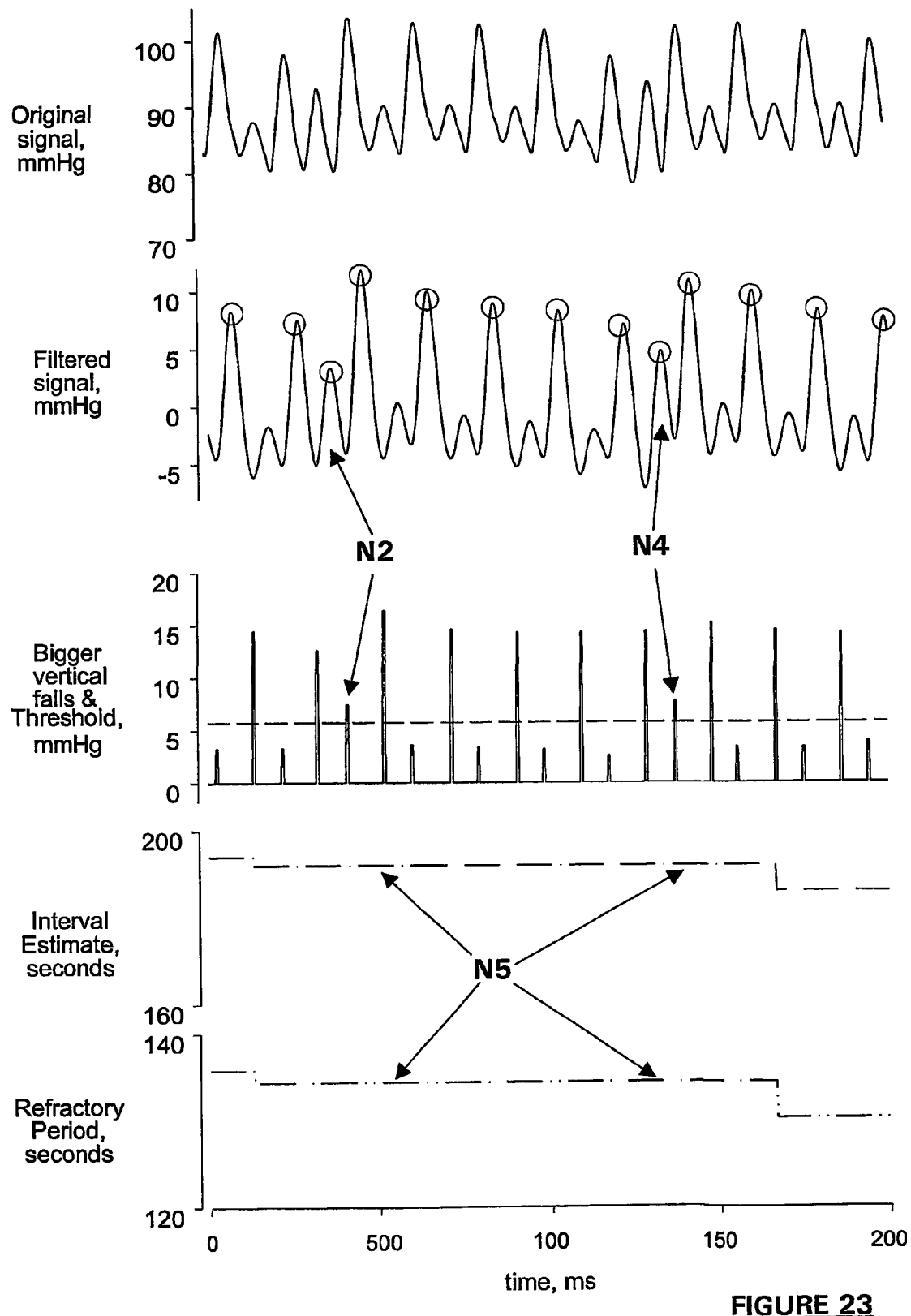
Figure 24:
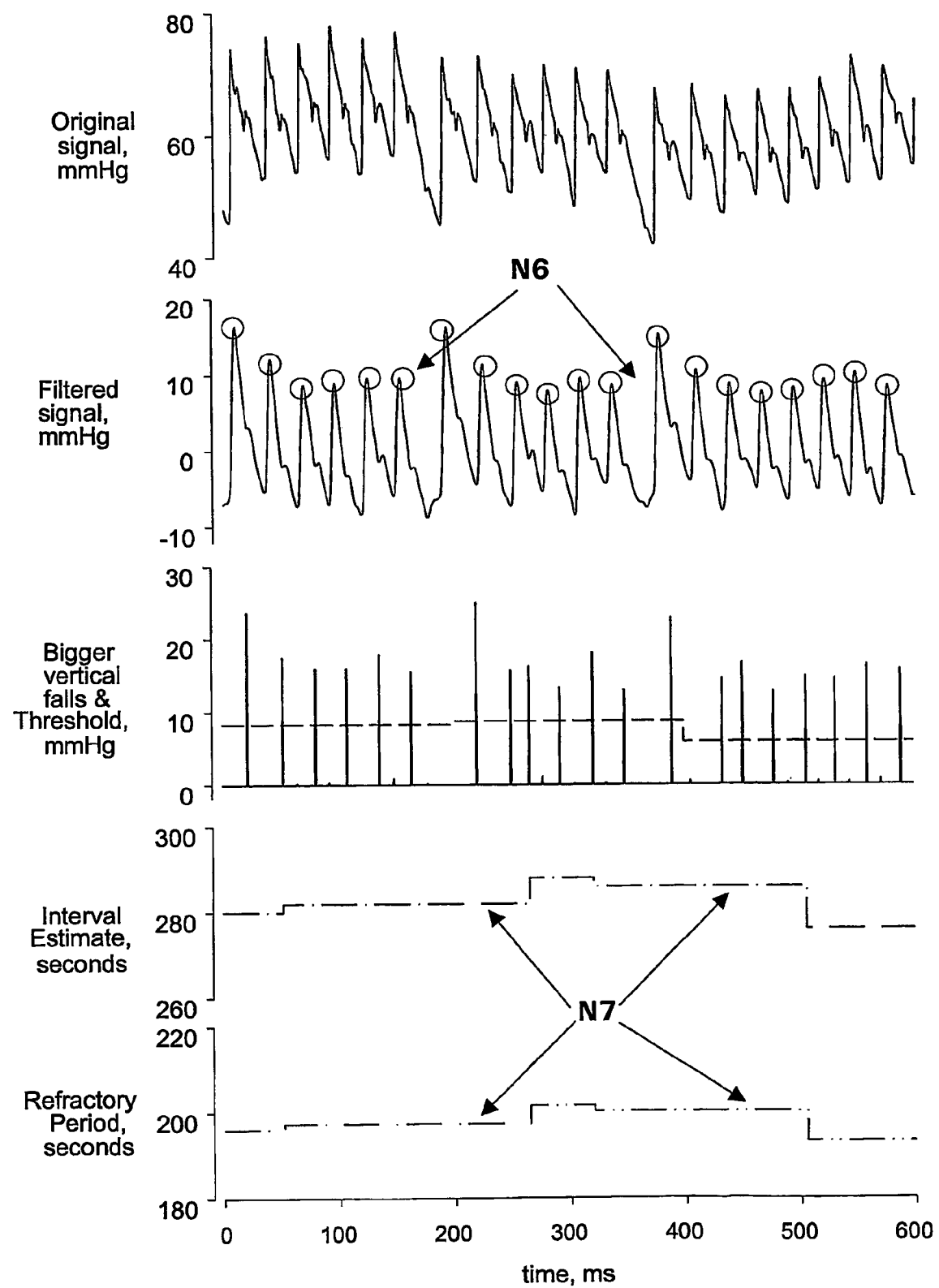
FIG. 24: shows a graphical example of the analysis of a filtered signal including unusually large intervals.
Figure 25:
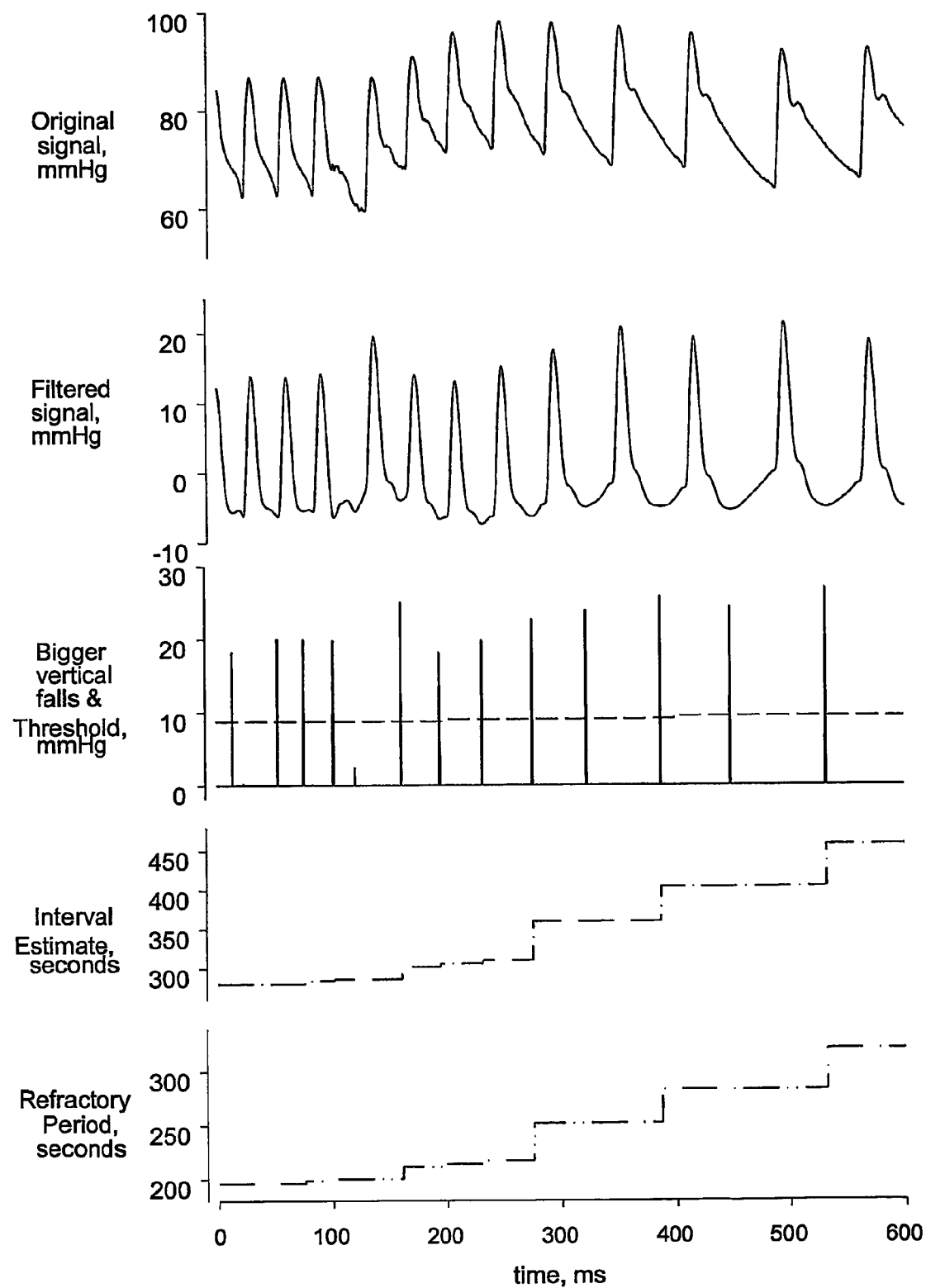
FIG. 25: shows a graphical example of the analysis of a filtered signal including a progressive decrease in frequency.
Figure 26:
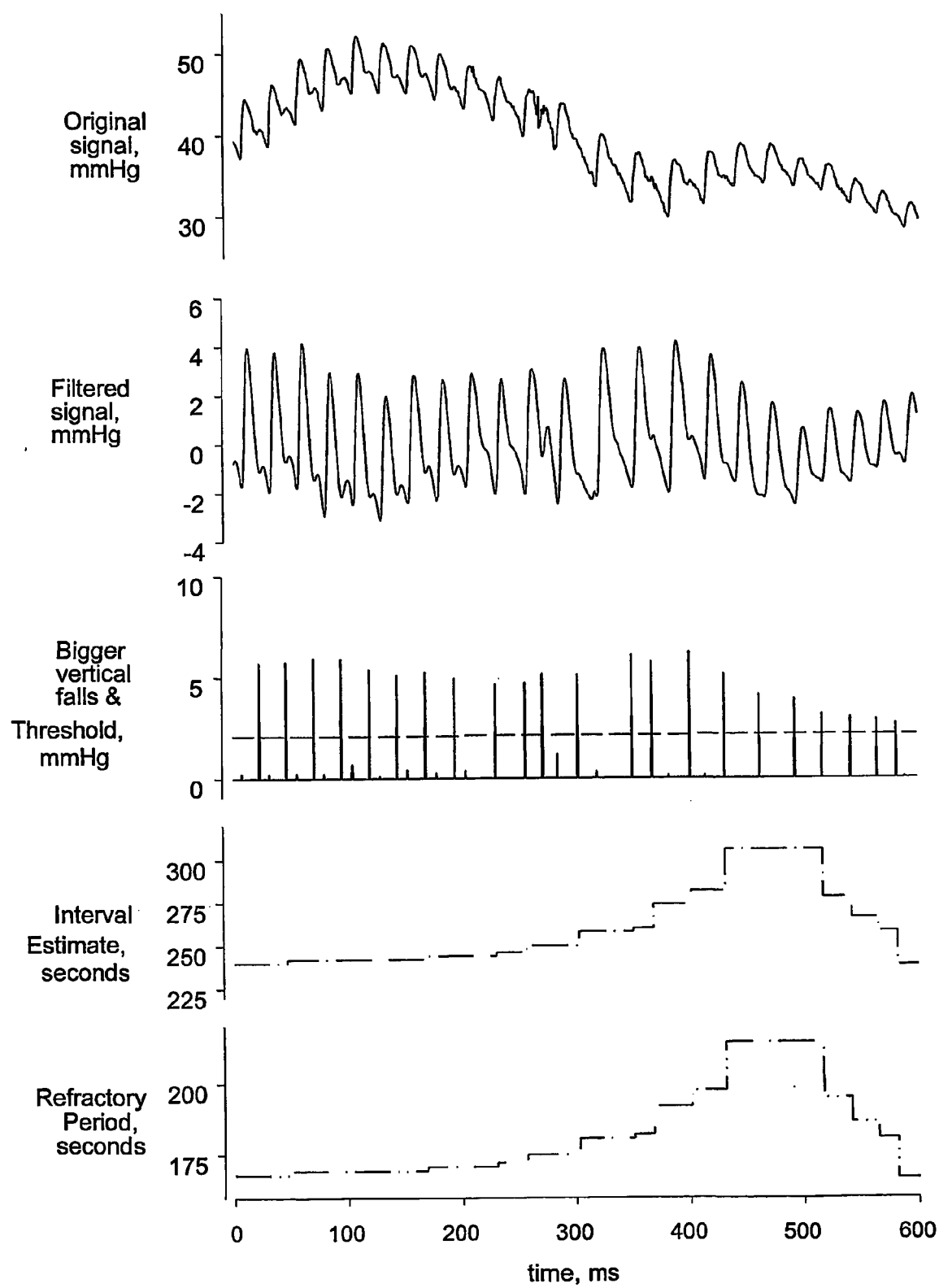
FIG. 26: shows a graphical example of the analysis of a signal including a large change in baseline and amplitude.

FIGS. 21-26 show graphical examples of the RP array calculations for various signals. FIG. 21 represents the case where a big notch in original signal is ignored because of the use of the bigger vertical side, see arrows N1. FIG. 22 shows the case where two big notches are not rejected and so four small intervals in row were determined, see arrows N2, which sharply reduced IE. But as RP is limited from below by 100 ms, it prevents a dramatic drop in RP, see the portion of the IE and RP plots marked with arrows N3. FIG. 23 shows the case where two big notches are not rejected by the threshold criterion, see arrows N4, but Interval Estimate ignores an appearance of two short (wrong) intervals because IE is calculated as the third lowest term in the last seven intervals ranked by magnitude, and thus RP is adequately calculated, see arrows N5. Other terms, such as the median may be used. FIG. 24 shows how periodically occurring, unusually big intervals, see arrows N6, are ignored for Interval Estimate and RP is calculated adequately, see arrows N7. FIG. 25 demonstrates how an increase in interval between maxima is followed by an increase in RP. In FIG. 26 the change in RP is following the change in an interval between maxima despite of the change in maxima amplitudes and fluctuating baseline.

Final detection includes the steps within box D of FIG. 13 and like the first embodiment includes the analysis of the original signal by means of producing two moving averages, a fast and slow moving average with shorter and longer averaging time interval. A 40 ms and 100 ms averaging time interval has been found suitable for the examples herein. The pilot value for the slow moving average might again be the shortest interval between signal peaks (100 ms for 600 beat per mean in rabbit), and the fast averaging interval 2-3 times shorter. The point where fast (F) moving average becomes bigger, than slow (S) moving average is determined as a before peak intersection (BPI) of the moving averages. The point where fast moving average becomes smaller, than slow moving average is determined as an after peak intersection (API) of the moving averages.

Figure 27:
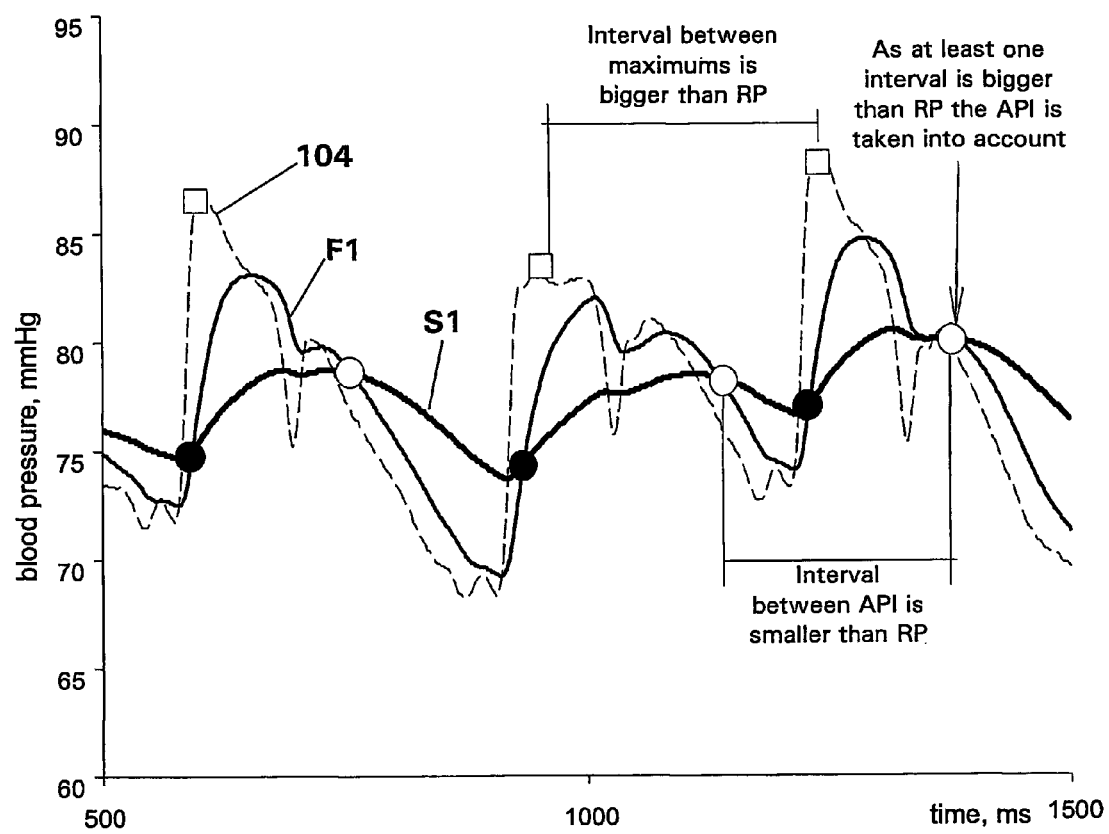
FIG. 27: shows a plot of an observed signal and a fast and slow moving average.

The API is equivalent to the APCP of the first embodiment, the change in terminology simply included to clarify the two alternative embodiments. The real peak is determined as the maximum value between successive crossing points BPI and API, if the last API comes after RP since previous API has elapsed, or the last maximum comes after the RP has elapsed since previous real peak maximum. FIG. 27 shows a typical detection situation with: an original signal 104; slow moving average S1; fast moving average F1; BPI, marked with a solid circle; API, marked with a hollow circle; and some peaks marked with a square determined.

It will be appreciated by those skilled in the art that the RP could be defined relative to the BPI rather than the API if required. Alternatively, the RP could be defined relative to both the BPI and API, for example at a predetermined location in time from the midpoint between the BPI and API. The important factor in locating the RP is to locate the RP where it is anticipated that false readings are probable or possible. In the case of a blood pressure waveform, this is the area following the notch, which occurs sometime close after a true or valid maximum.

The use of the API or BPI (or APCP in the first embodiment) is to define a fixed measurement period, or sample of the signal for analysis. In a further alternative form, the system may use the intersection of the original signal with a moving average to define intersections or crossing points suitable for defining a measurement period. Other suitable methods of defining measurement periods will be apparent to those skilled in the art.

Figure 28:
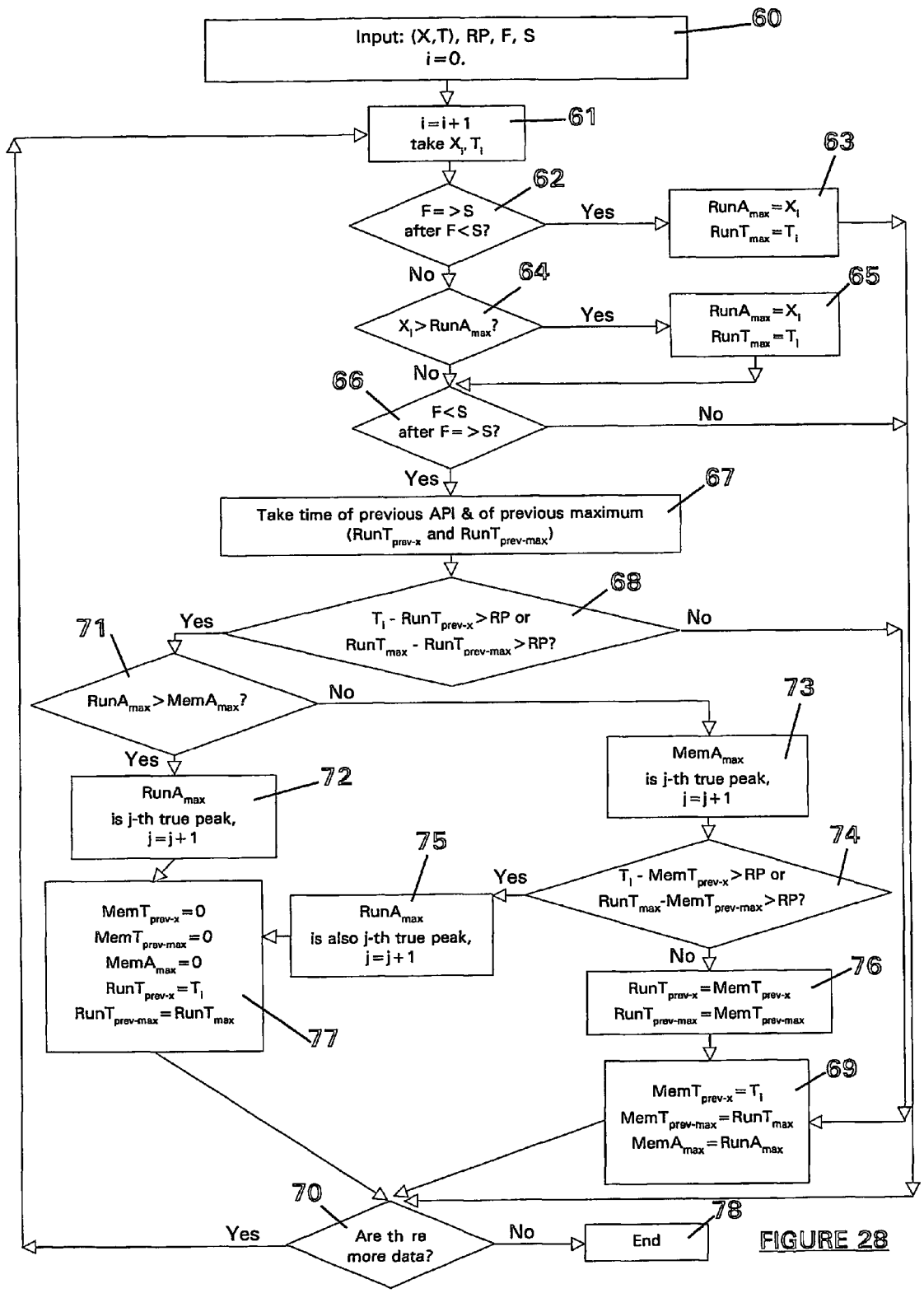
FIG. 28: shows a flow diagram of a final peak detection process according to the present invention.

FIG. 28 shows a flow diagram of the final peak detection process according to the second embodiment of the invention. Step 60 includes the input of the data pairs (X,T) showing the variation over time of the amplitude of the waveform, the array of RP values from step 56 (see FIG. 13) and the result of a computation of a fast moving average, F1 and a slow moving average S1. A loop counter, i is set to i=0.

In step 61, a data pair $(X_i, T_i)$ is taken and the loop counter incremented. The process involves monitoring the values of F1 and S1 in step 62 to indicate a BPI. After detection of a BPI and between detection of a BPI and API, the maximum of the observed signal is monitored and recorded as ($RunA_{max}$, $RunT_{max}$) in steps 64 and 65.

If a BPI is detected, the values of $RunA_{max}$ and $RunT_{max}$ are replaced by the values of (X, T) at the time of the BPI in step 63. Provided there is more data $(X_i, T_i)$, then the next data pair is taken. The maximum after the BPI is then monitored in steps 64 and 65 until the next API (the process cycles though steps 66, 70, 61 and 62 if there is a local minimum after the BPI prior to the next API). Once the next API is detected in step 66, the process proceeds to step 67.

In step 67, the values of the time of the previous API, $RunT_{prev-x}$ and time of the previous maximum, $RunT_{prev-max}$, which is associated with the previous API is taken. The time difference between the current API and previous API and between the current and previous maximum is computed and compared to the value of RP in step 68. If neither time difference is greater than RP, then the process proceeds to step 69, where the current running values are passed to memory. Provided there is more data, the process iterates back to step 61.

If either time difference computed in step 68 is greater than RP, in step 71 the value of the current maximum is compared with the memorised maximum which occurred within the RP, if any. If the current maximum is greater than the memorised maximum, the current maximum, which was stored as $RunA_{max}$ and $RunT_{max}$ in step 65, is identified as a valid maximum. An interval counter j is incremented, the values of the memorised maximums set to zero and the value and time of the identified maximum is stored as the value of the previous maximum for use in analysing the next maximum. This process is shown in FIG. 28 as steps 72 and 77. The process then iterates if there is more data (see step 70).

If in step 71 the value of the maximum held in memory is greater than the current maximum, the process proceeds to step 73 and the maximum held in memory is determined as a true maximum. The process then evaluates whether the current maximum is a true maximum by establishing whether it falls within the RP of the memorised maximum which has just been determined to be a true maximum in step 73. Thus, if the time difference between the API of the current maximum and the API of the memorised maximum or the time difference between the current maximum and previous maximum is greater than RP, then the current maximum is determined to also be a true maximum, see steps 74 and 75.

If the current maximum falls within the RP of the memorised maximum, then the memorised maximum becomes the previous maximum, with the times of the maximum and API corresponding to the maximum stored as $RunT_{prev-max}$ and $RunT_{prev-x}$ respectively, see steps 74 and 76. Next, in step 69, the current maximum is stored as the memorised maximum for comparison with the next maximum and associated API.

At the end of the data input, the process ends at step 78.

Figure 29:
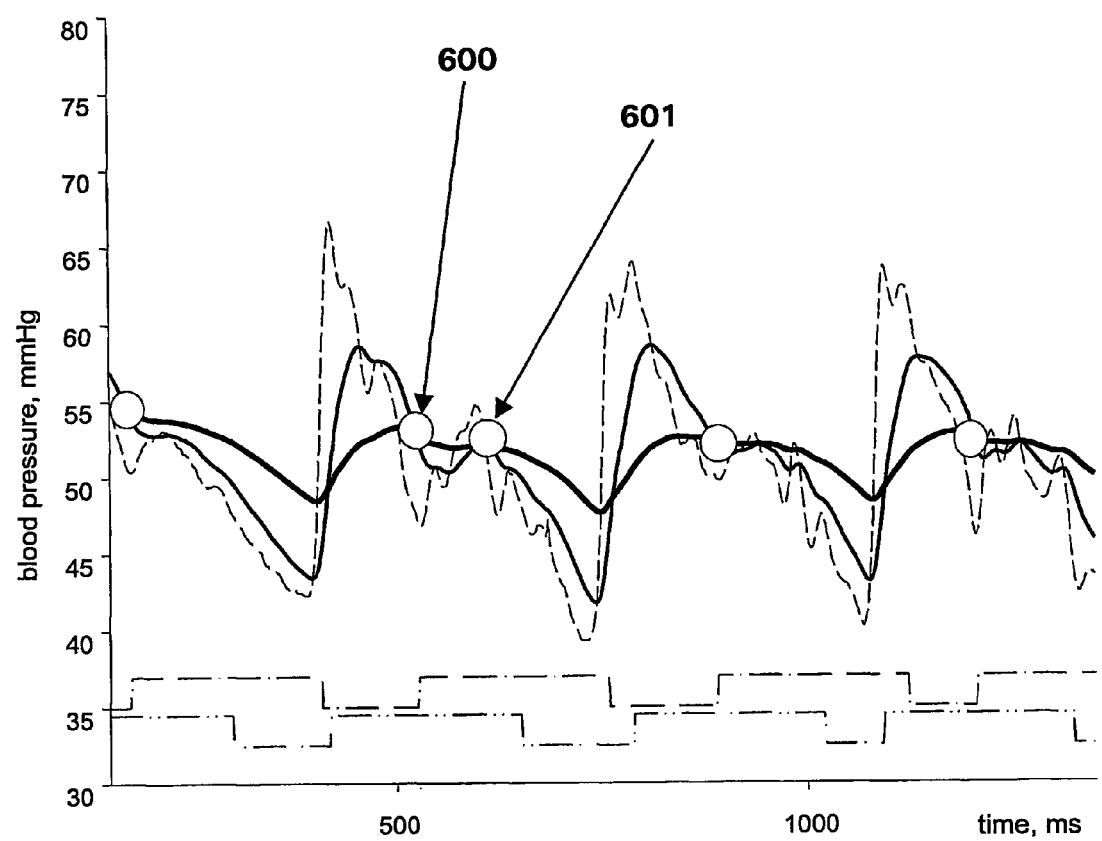
FIG. 29: shows a plot of an observed signal and a fast and slow moving average and the onset of the refractory periods for a signal which results in irregular intersections of moving averages.
Figure 30:
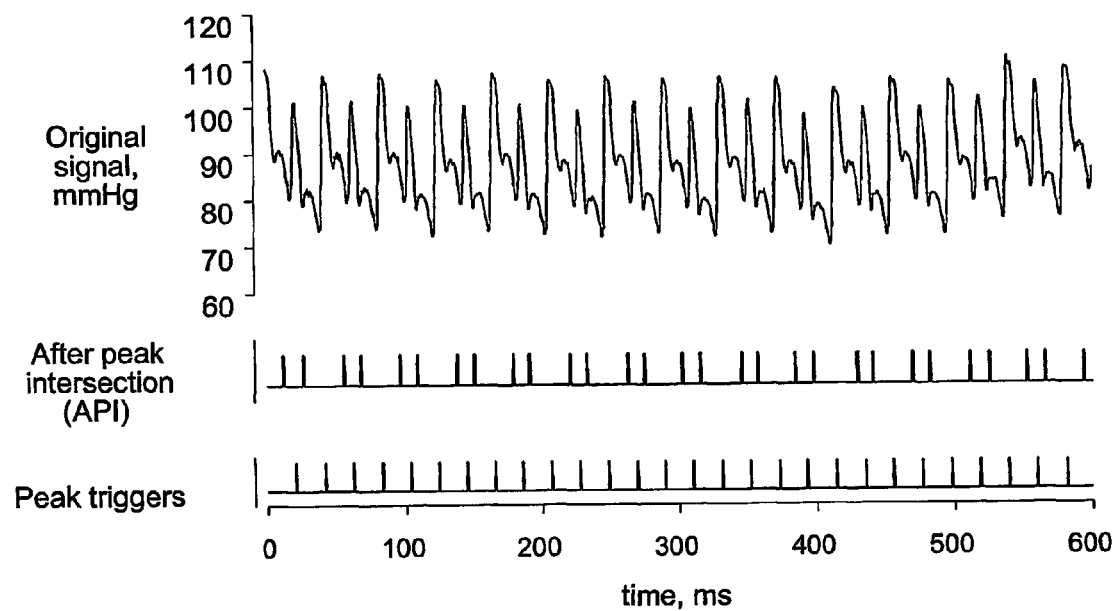
FIG. 30: shows an example of another waveform which results in irregular intersections of moving averages.
Figure 31:
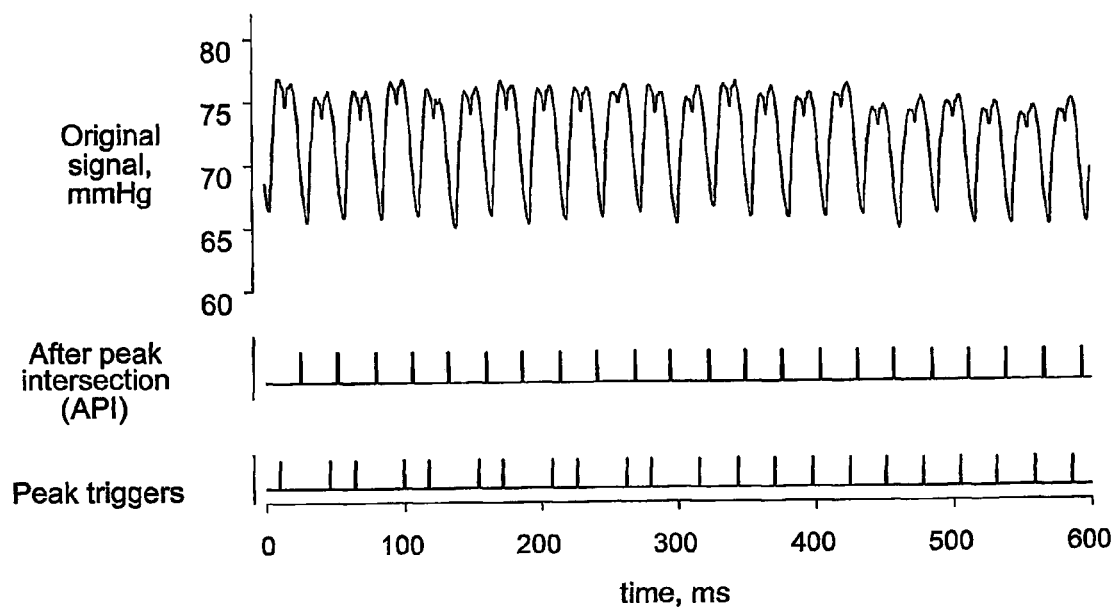
FIG. 31: shows an example of a waveform with irregular maxima location within each period.

The second embodiment may be preferred in many applications due to possible advantages in accuracy. The use of RP for two, instead of one characteristic point of the waveform may provide more stability to the algorithm. This occurs because in some cases intervals between intersections of moving averages are irregular, for example in the waveforms as shown in FIGS. 29 and 30. In this case, intersection 600 is taken into account, but intersection 601, is ignored because it came within the RP and the interval between the API corresponding to maximum 601 was within the RP from the API corresponding to maximum 600 and the maximum associated with API 601 was within the RP corresponding to the maximum associated with API 600. Also, in some cases the position of the peak maximum is irregular (see example in FIG. 31).

The algorithm in the second embodiment is not searching for the maximum between successive API, but in more narrow fashion between BPI and API. Therefore, if a baseline is fluctuating considerably, it may happen that a previous API will be higher than a current maximum, which may result in a false detection in the first embodiment.

The algorithm in the second embodiment is comparing the peak rejecfed as appeared within RP, with a peak lying outside the RP, and if the former is bigger it is taken as a true peak. This approach helps prevent the algorithm to be occasionally trapped in constantly detecting regularly spaced big notches while rejecting the true peaks lying within RP of notches.

For input signals that have markedly different wavelengths, variations may be made to algorithm to accommodate the different signals. In the second embodiment, calculation of the fast and slow moving averages may be changed depending of the wavelength. The averages may be made proportional to the interval estimate (IE) to allow automatic recalculation of the averaging intervals.

In addition, the upper an lower limit of the refractory period (RP) may be adjusted to suit a higher or lower expected wavelength. The pass-band of the filters may require adjustment. In the second embodiment, the sample size when determining the larger fall side may need to be increased for signals of larger wavelength. As the wavelength/heat rate is generally approximately known prior to measurement, these changes may be done manually. However, if required an algorithm may be developed to allow automatic calibration of the system.

After the location in time and amplitude of peaks in the original signal have been determined using the above described process, other parameters may be detected between peaks, such as the troughs of the signal, as well as the peaks and the troughs of the first derivative of the signal if required. Also, the frequency of the periodic signal follows immediately as the inverse of the interval between valid maxima.

The method may be implemented as an algorithm written in LabVIEW™ graphical programming language (National Instruments™, Austin, Tex., USA). The algorithm may also be implemented using other programming languages or may alternatively be implemented in a dedicated hardware system or a hybrid of a software and hardware implementation.

Where in the foregoing description, reference has been made to specific components or integers of the invention having known equivalents then such equivalents are herein incorporated as if individually set forth.

Although this invention has been described by way of example and with reference to possible embodiments thereof, it is to be understood that modifications or improvements may be made thereto without departing from the scope of the invention as defined in the appended claims.

What is claimed is:

1. A method of determining the frequency or period of a heartbeat, the method including the steps of:
    a) using a sensor to generate an electrical oscillatory signal representative of variation of the heartbeat, and using a computing apparatus to:
    b) observe the oscillatory signal by detecting the amplitude of the oscillatory signal;
    c) compute a first and a second moving average of the oscillatory signal, the first moving average having a first averaging time interval and the second moving average having a second averaging time interval longer than the first averaging time interval;
    d) determine the location in time of a plurality of crossing points, wherein a crossing point is a point of intersection between the first and second moving averages;
    e) define at least one measurement period as the interval between two crossing points; and
    f) determine the location in time of an absolute maximum or minimum of the oscillatory signal within the or each measurement period; and
    g) use the location in time of an absolute maximum from step f) to determine the frequency or period of the heartbeat.

2. The method of claim 1, wherein a crossing point is defined as a first type if the first moving average was less than the second moving average prior to the crossing point and defined as a second type if the first moving average was greater than the second moving average prior to the crossing point and wherein the measurement period is defined as the interval between two consecutive crossing points of the same type.

3. The method of claim 1, wherein a crossing point is defined as a first type if the first moving average was less than the second moving average prior to the crossing point and defined as a second type if the first moving average was greater than the second moving average prior to the crossing point and wherein the measurement period is defined as the interval between two consecutive crossing points of a different type.

4. The method of claim 1, further including the steps of:
    h) defining an exclusion period located in time relative to at least one of each crossing point defining each measurement period;
    i) evaluating whether a crossing point defining a first measurement period falls within an exclusion period corresponding to a crossing point defining a second measurement period; and
    j) if the crossing point defining the first measurement period falls within the exclusion period corresponding to the crossing point defining the second measurement period, evaluating whether that crossing point or the crossing point corresponding to the exclusion period within which it is located in time satisfies a first predetermined set of criteria and rejecting the crossing point for the purposes of defining a measurement period if said criteria are met.

5. The method of claim 4, wherein if a crossing point is rejected, the method further includes also rejecting the exclusion period associated with the rejected crossing point.

6. The method of claim 4, further including the steps of using the computing apparatus to:
    k) detect the location in time of a plurality of local maxima or minima within the oscillatory signal that exceed a predetermined amplitude threshold; and
    l) compute the length of the exclusion period in time dependent on an average value of the separation in time of detected maxima or minima that exceed said predetermined amplitude threshold.

7. The method of claim 6, further including rejecting a local maximum detected in step k) for the purposes of step l) if the local maximum falls within a predetermined time period of a local maximum having a greater value.

8. The method of claim 6, further including rejecting a local minimum detected in step k) for the purposes of step l) if the local minimum falls within a predetermined time period of a local minimum having a lesser value.

9. The method of claim 6, wherein said average value of the separation in time of detected maxima or minima is the median value.

10. The method of claim 6, further including band-pass filtering the electrical oscillatory signal prior to performing step k).

11. The method of claim 6, wherein the predetermined amplitude threshold is computed using the equation: $Thr = (Max_F - Avg_F) \cdot f_1 + Avg_F$ if maxima is determined in step f) and using the equation $Thr = (Min_F - Avg_F) \cdot f_1 + Avg_F$ if minima is determined in step f), wherein Thr is the predetermined threshold, $Avg_F$ is an average of the observed signal, $Max_F$ is the maximum of the observed signal, $Min_F$ is the minimum of the observed signal, and $f_1$ is a preset fraction dependent on the characteristics of the electrical oscillatory signal and wherein $Avg_F$, $Max_F$, and $Min_F$ are determined from a sample of the electrical oscillatory signal.

12. The method of claim 4, wherein step h) comprises locating the exclusion period immediately adjacent to the crossing point after the crossing point.

13. The method of claim 4, wherein the set of predetermined criteria is based on the relative magnitude of a maximum or minimum in an exclusion period to the magnitude of at least one maximum or minimum respectively in the observed signal.

14. The method of claim 13, wherein a crossing point is rejected if the amplitude of a maximum within the measurement period defined by that crossing point is less than an adjacent maximum or less than a predetermined percentage of an adjacent maximum.

15. The method of claim 13, wherein a crossing point is rejected if the amplitude of the corresponding minimum to the crossing point located within the exclusion period is greater than an adjacent minimum or greater than a percentage of an adjacent minimum.

16. The method of claim 4, further including:
defining an exclusion period located in time relative to a detected maximum or minimum within each measurement period; and
evaluating whether a detected maximum or minimum of a first measurement period falls within an exclusion period corresponding to a maximum or minimum of a second measurement period; and
if the maximum or minimum of the first measurement period falls within the exclusion period of the second measurement period, evaluating whether the crossing point corresponding to the maximum or minimum of the first measurement period or the crossing point corresponding to the exclusion period within which the maximum or minimum of the first measurement period falls satisfies a predetermined set of criteria and rejecting a crossing point for the purposes of defining a measurement period if said criteria are met;
wherein a crossing point is rejected only if it is within an exclusion period corresponding to another crossing point and the maximum or minimum corresponding to the crossing point is within an exclusion period corresponding to another maximum or minimum.

17. The method of claim 1, further including comparing an average value of the electrical oscillatory signal over a sample period with the maximum and minimum values over the same sample period and inverting the electrical oscillatory signal if required so that the maximum or minimum determined in step f) has a greater variation from the average than the minimum or maximum respectively.

18. The method of claim 17, wherein the reflected or inverted signal is computed as double an average of the electrical oscillatory signal less the value of the electrical oscillatory-signal.

19. The method of claim 1, further including using the computing apparatus to:
define an exclusion period located in time relative to a detected maximum or minimum within each measurement period; and
evaluate whether a detected maximum or minimum of a first measurement period falls within an exclusion period corresponding to a maximum or minimum of a second measurement period; and
if the maximum or minimum of the first measurement period falls within the exclusion period of the second measurement period, evaluate whether the crossing point corresponding to the maximum or minimum of the first measurement period or the crossing point corresponding to the exclusion period within which the maximum or minimum of the first measurement period falls satisfies a predetermined set of criteria and reject a crossing point for the purposes of defining a measurement period if said criteria are met.

20. The method of claim 19, wherein the set of predetermined criteria is based on the relative magnitude of a maximum or minimum in an exclusion period to the magnitude of at least one maximum or minimum respectively in the electrical oscillatory signal.

21. The method of claim 20, wherein a crossing point is rejected if the amplitude of a maximum within the measurement period defined by that crossing point is less than an adjacent maximum or less than a predetermined percentage of an adjacent maximum.

22. The method of claim 20, wherein a crossing point is rejected if the amplitude of the corresponding minimum to the crossing point located within the exclusion period is greater than an adjacent minimum or greater than a percentage of an adjacent minimum.

23. The method of claim 1, further including the step of recording the maximum or minimum value of the oscillatory signal in each measurement period.

24. A method of determining the frequency or period of a heartbeat, comprising determining the location in time of maxima and/or minima of the heartbeat by the method according to claim 1, calculating the difference in time between maxima and/or minima, and using said difference in time to calculate the frequency and/or period of the heartbeat.

25. A method of claim 1, when performed in real-time wherein the location in time of periodic maxima and/or minima of an oscillatory signal is determined in real time.

26. Apparatus for determining the frequency or period of a heartbeat, the apparatus including sensing means to generate an electrical oscillatory signal representative of variation of the heartbeat and a computer processing means in communication with the sensing means and having an instruction set to cause said computer processing means to:
a) detect the amplitude of the oscillatory signal;
b) compute a first and a second moving average of the oscillatory signal, the first moving average having a first averaging time interval and the second moving average having a second averaging time interval longer than the first averaging time interval;
c) compute the location in time of a plurality of crossing points, wherein a crossing point is a point of intersection between the first and second moving averages;
d) define at least one measurement period as the interval between two crossing points;
e) compute the location in time of an absolute maximum or minimum of the oscillatory signal within the or each measurement period, and;
f) use the location in time of an amplitude maximum or minimum to determine the frequency or period of the heartbeat system.

* * * * *